(12) United States Patent
Burnett

(10) Patent No.: US 9,066,186 B2
(45) Date of Patent: Jun. 23, 2015

(54) LIGHT-BASED DETECTION FOR ACOUSTIC APPLICATIONS

(75) Inventor: Gregory C. Burnett, Northfield, MN (US)

(73) Assignee: AliphCom, San Francisco, CA (US)

( * ) Notice: Subject to any disclaimer, the term of this patent is extended or adjusted under 35 U.S.C. 154(b) by 283 days.

(21) Appl. No.: 13/420,568

(22) Filed: Mar. 14, 2012

(65) Prior Publication Data

US 2012/0230699 A1   Sep. 13, 2012

Related U.S. Application Data

(63) Continuation-in-part of application No. 12/139,333, filed on Jun. 13, 2008, now Pat. No. 8,503,691, and a continuation-in-part of application No. 12/243,718, filed on Oct. 1, 2008, now Pat. No. 8,130,984, (Continued)

(51) Int. Cl.
*H04R 25/00* (2006.01)
*H04R 23/00* (2006.01)
*G10L 21/0208* (2013.01)

(Continued)

(52) U.S. Cl.
CPC .............. *H04R 23/008* (2013.01); *A61B 5/6815* (2013.01); *G10L 21/0208* (2013.01); *G10L 2021/02165* (2013.01); *H04R 1/1008* (2013.01); *H04R 1/1083* (2013.01); *H04R 1/406* (2013.01); *H04R 3/005* (2013.01); *H04R 3/04* (2013.01); *H04R 1/46* (2013.01)

(58) Field of Classification Search
CPC ................... A61N 2005/0651; A61N 5/6815; H04R 1/1083; G10L 21/0208
USPC .......................................................... 381/151
See application file for complete search history.

(56) References Cited

U.S. PATENT DOCUMENTS

| 2,121,779 A | 6/1938 | Ballantine |
| 3,789,166 A | 1/1974 | Sebesta |

(Continued)

FOREIGN PATENT DOCUMENTS

| EP | 0637187 A2 | 2/1995 |
| EP | 795851 A2 | 9/1997 |

(Continued)

OTHER PUBLICATIONS

U.S. Appl. No. 12/772,963, filed May 3, 2010, Petit et al.
Burnett et al., U.S. Appl. No. 14/225,339, filed Mar. 25, 2014.
Asseily et al., U.S. Appl. No. 10/769,302, filed Jan. 30, 2004.
Burnett, U.S. Appl. No. 12/163,617, filed Jun. 27, 2008.
Burnett, U.S. Appl. No. 12/163,647, filed Jun. 27, 2008.
Burnett, U.S. Appl. No. 12/163,675, filed Jun. 27, 2008.

(Continued)

*Primary Examiner* — Howard Weiss
(74) *Attorney, Agent, or Firm* — Kokka & Backus, PC

(57) ABSTRACT

A light-based skin contact detector is described, including a boot having an index of refraction less than or equal to another index of refraction associated with skin at a frequency of light, a light emitter and detector coupled to the boot and configured to measure an amount of light energy reflected by an interface of the boot, and a digital signal processor configured to detect a change in the amount of light energy reflected by the interface. Embodiments relate to methods for detecting skin contact by measuring an amount of energy reflected by an interface when a boot is not in contact with skin, measuring another amount of energy reflected by another interface when the boot is in contact with the skin, and detecting a change between the amount of energy and the another amount of energy using a digital signal processor.

16 Claims, 29 Drawing Sheets

Related U.S. Application Data application No. 13/420,568, which is a continuation-in-part of application No. 10/769,302, filed on Jan. 30, 2004, now Pat. No. 7,443,484.

(60) Provisional application No. 61/452,948, filed on Mar. 15, 2011, provisional application No. 60/934,551, filed on Jun. 13, 2007, provisional application No. 60/953,444, filed on Aug. 1, 2007, provisional application No. 60/954,712, filed on Aug. 8, 2007, provisional application No. 61/045,377, filed on Apr. 16, 2008, provisional application No. 60/443,818, filed on Jan. 30, 2003.

(51) Int. Cl.
| | |
|---|---|
| H04R 1/40 | (2006.01) |
| H04R 3/00 | (2006.01) |
| H04R 3/04 | (2006.01) |
| H04R 1/46 | (2006.01) |
| A61B 5/00 | (2006.01) |
| G10L 21/0216 | (2013.01) |
| H04R 1/10 | (2006.01) |

(56) References Cited

U.S. PATENT DOCUMENTS

| | | |
|---|---|---|
| 4,006,318 A | 2/1977 | Sebesta et al. |
| 4,012,604 A | 3/1977 | Speidel |
| 4,521,908 A | 6/1985 | Miyaji et al. |
| 4,591,668 A | 5/1986 | Iwata |
| 4,607,383 A | 8/1986 | Ingalls |
| 4,653,102 A | 3/1987 | Hansen |
| 4,777,649 A | 10/1988 | Carlson et al. |
| 4,901,354 A | 2/1990 | Gerhard et al. |
| 4,949,387 A | 8/1990 | Andert et al. |
| 5,097,515 A | 3/1992 | Baba |
| 5,150,418 A | 9/1992 | Honda et al. |
| 5,205,285 A | 4/1993 | Baker, Jr. |
| 5,208,864 A | 5/1993 | Kaneda |
| 5,212,764 A | 5/1993 | Ariyoshi |
| 5,276,765 A | 1/1994 | Freeman |
| 5,353,376 A | 10/1994 | Oh et al. |
| 5,400,409 A | 3/1995 | Linhard |
| 5,406,622 A | 4/1995 | Silverberg et al. |
| 5,414,776 A | 5/1995 | Sims, Jr. |
| 5,459,814 A | 10/1995 | Gupta et al. |
| 5,463,694 A | 10/1995 | Bradely et al. |
| 5,473,701 A | 12/1995 | Cezanne et al. |
| 5,473,702 A | 12/1995 | Yoshida et al. |
| 5,515,865 A | 5/1996 | Scanlon et al. |
| 5,517,435 A | 5/1996 | Sugiyama |
| 5,539,859 A | 7/1996 | Robbe et al. |
| 5,590,241 A | 12/1996 | Park et al. |
| 5,625,684 A | 4/1997 | Matouk et al. |
| 5,633,935 A | 5/1997 | Kanamori et al. |
| 5,649,055 A | 7/1997 | Gupta et al. |
| 5,664,014 A | 9/1997 | Yamaguchi et al. |
| 5,664,052 A | 9/1997 | Nishiguchi et al. |
| 5,675,655 A | 10/1997 | Hatae |
| 5,684,460 A | 11/1997 | Scanlon et al. |
| 5,729,694 A | 3/1998 | Holzrichter et al. |
| 5,754,665 A | 5/1998 | Hosoi |
| 5,790,684 A | 8/1998 | Niino et al. |
| 5,796,842 A | 8/1998 | Hanna |
| 5,815,582 A | 9/1998 | Claybaugh et al. |
| 5,825,897 A | 10/1998 | Andrea et al. |
| 5,835,608 A | 11/1998 | Warnaka et al. |
| 5,853,005 A | 12/1998 | Scanlon |
| 5,907,624 A | 5/1999 | Takada |
| 5,917,921 A | 6/1999 | Sasaki et al. |
| 5,966,090 A | 10/1999 | McEwan |
| 5,986,600 A | 11/1999 | McEwan |
| 6,000,396 A | 12/1999 | Nagata |
| 6,006,175 A | 12/1999 | Holzrichter |
| 6,069,963 A | 5/2000 | Martin et al. |
| 6,173,059 B1 | 1/2001 | Huang et al. |
| 6,188,773 B1 | 2/2001 | Murata et al. |
| 6,191,724 B1 | 2/2001 | McEwan |
| 6,233,551 B1 | 5/2001 | Cho et al. |
| 6,266,422 B1 | 7/2001 | Ikeda |
| 6,408,079 B1 | 6/2002 | Katayama |
| 6,430,295 B1 | 8/2002 | Handel et al. |
| 6,448,488 B1 | 9/2002 | Ekhaus et al. |
| 6,473,733 B1 | 10/2002 | McArthur et al. |
| 6,618,485 B1 | 9/2003 | Matsuo |
| 6,668,062 B1 | 12/2003 | Luo et al. |
| 6,685,638 B1 | 2/2004 | Taylor et al. |
| 6,707,910 B1 | 3/2004 | Valve et al. |
| 6,717,991 B1 | 4/2004 | Gustafsson et al. |
| 6,766,292 B1 | 7/2004 | Chandran et al. |
| 6,771,788 B1 | 8/2004 | Soutar et al. |
| 6,795,713 B2 | 9/2004 | Housni |
| 6,816,469 B1 | 11/2004 | Kung et al. |
| 6,889,187 B2 | 5/2005 | Zhang |
| 6,963,649 B2 | 11/2005 | Vaudrey et al. |
| 6,980,092 B2 | 12/2005 | Turnbull et al. |
| 7,020,291 B2 | 3/2006 | Buck et al. |
| 7,120,261 B1 | 10/2006 | Turnbull et al. |
| 7,146,013 B1 | 12/2006 | Saito et al. |
| 7,171,357 B2 | 1/2007 | Boland |
| 7,203,328 B2 | 4/2007 | Beimel et al. |
| 7,206,418 B2 | 4/2007 | Yang et al. |
| 7,246,058 B2 | 7/2007 | Burnett |
| 7,386,135 B2 | 6/2008 | Fan |
| 7,433,484 B2 | 10/2008 | Asseily et al. |
| 7,464,029 B2 | 12/2008 | Visser et al. |
| 7,617,099 B2 | 11/2009 | Yang et al. |
| 7,653,537 B2 | 1/2010 | Padhi et al. |
| 7,706,549 B2 | 4/2010 | Zhang et al. |
| 8,019,091 B2 | 9/2011 | Burnett et al. |
| 8,068,619 B2 | 11/2011 | Zhang et al. |
| 8,130,984 B2 | 3/2012 | Asseily et al. |
| 8,218,751 B2 | 7/2012 | Hepworth et al. |
| 8,254,617 B2 | 8/2012 | Burnett |
| 8,280,072 B2 | 10/2012 | Burnett |
| 8,321,213 B2 | 11/2012 | Petit et al. |
| 8,326,611 B2 | 12/2012 | Petit et al. |
| 8,452,023 B2 | 5/2013 | Petit et al. |
| 8,467,543 B2 | 6/2013 | Burnett et al. |
| 8,477,961 B2 | 7/2013 | Burnett |
| 8,488,803 B2 | 7/2013 | Yamamoto et al. |
| 8,494,177 B2 | 7/2013 | Burnett |
| 8,503,686 B2 | 8/2013 | Jing et al. |
| 8,503,691 B2 | 8/2013 | Burnett |
| 8,503,692 B2 | 8/2013 | Burnett |
| 8,682,018 B2 | 3/2014 | Burnett |
| 8,699,721 B2 | 4/2014 | Burnett |
| 8,700,111 B2 * | 4/2014 | LeBoeuf et al. ............ 600/310 |
| 8,731,211 B2 | 5/2014 | Burnett |
| 8,837,746 B2 | 9/2014 | Burnett |
| 8,838,184 B2 | 9/2014 | Burnett et al. |
| 2001/0028713 A1 | 10/2001 | Walker |
| 2002/0039425 A1 | 4/2002 | Burnett et al. |
| 2002/0110256 A1 | 8/2002 | Watson et al. |
| 2002/0116187 A1 | 8/2002 | Erten |
| 2002/0165711 A1 | 11/2002 | Boland |
| 2002/0198705 A1 | 12/2002 | Burnett |
| 2003/0016835 A1 | 1/2003 | Elko et al. |
| 2003/0044025 A1 | 3/2003 | Ouyang et al. |
| 2003/0130839 A1 | 7/2003 | Beaucoup et al. |
| 2003/0228023 A1 | 12/2003 | Burnett et al. |
| 2004/0052364 A1 | 3/2004 | Bodley et al. |
| 2004/0133421 A1 | 7/2004 | Burnett et al. |
| 2004/0165736 A1 | 8/2004 | Hetherington et al. |
| 2004/0167502 A1 * | 8/2004 | Weckwerth et al. ............ 606/9 |
| 2004/0167777 A1 | 8/2004 | Hetherington et al. |
| 2004/0249633 A1 | 12/2004 | Asseily et al. |
| 2004/0264706 A1 | 12/2004 | Ray et al. |
| 2005/0047611 A1 | 3/2005 | Mao |
| 2005/0071154 A1 | 3/2005 | Etter |
| 2005/0094795 A1 | 5/2005 | Rambo |
| 2005/0156753 A1 | 7/2005 | DeLine et al. |

(56) References Cited

U.S. PATENT DOCUMENTS

| | | |
|---|---|---|
| 2005/0157890 A1 | 7/2005 | Nakajima et al. |
| 2005/0213736 A1 | 9/2005 | Rodman et al. |
| 2005/0271220 A1 | 12/2005 | Bathurst et al. |
| 2005/0286696 A1 | 12/2005 | Bathurst et al. |
| 2005/0286697 A1 | 12/2005 | Bathurst et al. |
| 2006/0119837 A1 | 6/2006 | Raguin et al. |
| 2006/0147032 A1 | 7/2006 | McCree et al. |
| 2006/0147054 A1 | 7/2006 | Buck et al. |
| 2006/0215841 A1 | 9/2006 | Vieilledent et al. |
| 2006/0269080 A1 | 11/2006 | Oxford et al. |
| 2007/0003082 A1 | 1/2007 | Pedersen |
| 2007/0058822 A1 | 3/2007 | Ozawa |
| 2007/0121974 A1 | 5/2007 | Nemirovski |
| 2007/0149246 A1 | 6/2007 | Bodley et al. |
| 2007/0183610 A1 | 8/2007 | Kidmose |
| 2007/0233479 A1 | 10/2007 | Burnett |
| 2007/0257840 A1 | 11/2007 | Wang |
| 2008/0013749 A1 | 1/2008 | Konchitsky |
| 2008/0031474 A1 | 2/2008 | Berardi et al. |
| 2008/0084831 A1 | 4/2008 | Sylvain |
| 2008/0201138 A1 | 8/2008 | Visser et al. |
| 2008/0260175 A1 | 10/2008 | Elko |
| 2009/0003623 A1 | 1/2009 | Burnett |
| 2009/0003624 A1 | 1/2009 | Burnett |
| 2009/0003625 A1 | 1/2009 | Burnett |
| 2009/0003626 A1 | 1/2009 | Burnett |
| 2009/0003640 A1 | 1/2009 | Burnett |
| 2009/0010449 A1 | 1/2009 | Burnett |
| 2009/0010450 A1 | 1/2009 | Burnett |
| 2009/0010451 A1 | 1/2009 | Burnett |
| 2009/0022350 A1 | 1/2009 | Asseily et al. |
| 2009/0058611 A1 | 3/2009 | Kawamura et al. |
| 2009/0081999 A1 | 3/2009 | Khasawneh et al. |
| 2009/0089053 A1 | 4/2009 | Wang et al. |
| 2009/0154726 A1 | 6/2009 | Taenzer |
| 2009/0164212 A1 | 6/2009 | Chan et al. |
| 2009/0252351 A1 | 10/2009 | Rosener |
| 2009/0264114 A1 | 10/2009 | Virolainen et al. |
| 2009/0299739 A1 | 12/2009 | Chan et al. |
| 2010/0128881 A1 | 5/2010 | Petit et al. |
| 2010/0128894 A1 | 5/2010 | Petit et al. |
| 2010/0278352 A1 | 11/2010 | Petit |
| 2010/0280824 A1 | 11/2010 | Petit et al. |
| 2011/0026722 A1 | 2/2011 | Jing et al. |
| 2011/0051950 A1 | 3/2011 | Burnett |
| 2011/0051951 A1 | 3/2011 | Burnett |
| 2011/0129101 A1 | 6/2011 | Hooley |
| 2012/0059648 A1 | 3/2012 | Burnett |
| 2012/0184337 A1 | 7/2012 | Burnett et al. |
| 2012/0207322 A1 | 8/2012 | Burnett |
| 2012/0230511 A1 | 9/2012 | Burnett |
| 2012/0230699 A1 | 9/2012 | Burnett et al. |
| 2012/0288079 A1 | 11/2012 | Burnett et al. |
| 2013/0010982 A1 | 1/2013 | Elko et al. |
| 2013/0211830 A1 | 8/2013 | Petit et al. |
| 2014/0126743 A1 | 5/2014 | Petit et al. |
| 2014/0126744 A1 | 5/2014 | Petit et al. |
| 2014/0140524 A1 | 5/2014 | Petit |
| 2014/0140527 A1 | 5/2014 | Burnett |
| 2014/0177860 A1 | 6/2014 | Burnett |
| 2014/0185824 A1 | 7/2014 | Burnett |
| 2014/0185825 A1 | 7/2014 | Burnett |
| 2014/0188467 A1 | 7/2014 | Jing et al. |
| 2014/0294208 A1 | 10/2014 | Burnett et al. |

FOREIGN PATENT DOCUMENTS

| | | |
|---|---|---|
| EP | 0869697 | 7/1998 |
| EP | 0984660 A2 | 3/2000 |
| JP | 2000312395 A | 11/2000 |
| JP | 2001189987 A | 7/2001 |
| WO | 0207151 A | 1/2002 |
| WO | 02098169 A1 | 12/2002 |
| WO | 03083828 A1 | 10/2003 |
| WO | 03096031 A2 | 11/2003 |
| WO | 2004056298 | 7/2004 |
| WO | 2006/001960 A1 | 1/2006 |
| WO | 2007106399 A3 | 9/2007 |
| WO | 2008157421 | 12/2008 |
| WO | 2009003180 | 12/2008 |
| WO | 2010/002676 A2 | 1/2010 |
| WO | 2010048635 | 4/2010 |
| WO | 2011002823 | 1/2011 |
| WO | 2011140096 | 11/2011 |
| WO | 2011140110 A1 | 11/2011 |
| WO | 2012009689 | 1/2012 |
| WO | 2012125873 A2 | 9/2012 |

OTHER PUBLICATIONS

Petit et al., U.S. Appl. No. 12/606,140, filed Oct. 26, 2009.
Jing et al., U.S. Appl. No. 12/772,947, filed May 3, 2010.
Petit et al., U.S. Appl. No. 12/606,146, filed Oct. 26, 2009.
Burnett et al., U.S. Appl. No. 10/400,282, filed Mar. 27, 2003.
Gregory C. Burnett, U.S. Appl. No. 09/990,847, filed Nov, 21, 2001.
Jing et al., U.S. Appl. No. 13/959,709, filed Aug. 5, 2013.
Petit et al., U.S. Appl. No. 12/772,975, filed Mar. 3, 2010.
Burnett et al., U.S. Appl. No. 13/184,422, filed Jul. 15, 2011.
Gregory C. Burnett, U.S. Appl. No. 13/431,725, filed Mar. 27, 2012.
Gregory C. Burnett, U.S. Appl. No. 13/959,707, filed Aug. 5, 2013.
Gregory C. Burnett, U.S. Appl. No. 10/301,237, filed Nov. 21, 2002.
Petit et al., U.S. Appl. No. 13/942,674, filed Jul. 15, 2013.
Gregory C. Burnett, U.S. Appl. No. 12/826,643, filed Jun. 29, 2010.
Gregory C. Burnett, U.S. Appl. No. 12/826,658, filed Jun. 29, 2010.
Gregory C. Burnett, U.S. Appl. No. 13/929,718, filed Jun. 27, 2013.
Gregory C. Burnett, U.S. Appl. No. 12/163,592, filed Jun. 27, 2008.
Burnett et al., U.S. Appl. No. 14/488,042, filed Sep. 16, 2014.
Gregory C. Burnett, U.S. Appl. No. 14/224,868, filed Mar. 25, 2014.
Gregory C. Burnett, U.S. Appl. No. 12/139,361, filed Jun. 13, 2008.
Gregory C. Burnett, U.S. Appl. No. 13/948,160, filed Jul. 22, 2013, 7.
Gregory C. Burnett, U.S. Appl. No. 12/139,355, filed Jun. 13, 2008.
Gregory C. Burnett, U.S. Appl. No. 12/139,344, filed Jun. 13, 2008.
Gregory C. Burnett, U.S. Appl. No. 13/959,708, Aug. 5, 2013.
Gregory C. Burnett, U.S. Appl. No. 12/139,333, filed Jun. 13, 2008.
Gregory C. Burnett, U.S. Appl. No. 13/436,765, filed Mar. 30, 2012.
Gregory C. Burnett, U.S. Appl. No. 11/805,987, filed May 25, 2007.
Burnett et al., U.S. Appl. No. 10/383,162, filed Mar, 5, 2003.
Burnett et al., U.S. Appl. No. 10/667,207,filed Sep. 18, 2003.
Burnett et al., U.S. Appl. No. 09/905,361, filed Jul. 12, 2001.
Gregory C. Burnett, U.S. Appl. No. 14/270,242, filed May 5, 2014.
Gregory C. Burnett, U.S. Appl. No. 14/270,249, filed May 5, 2014.
Burnett et al., U.S. Appl. No. 13/184,429, filed Jul. 15, 2011.
Petit et al., U.S. Appl. No. 13/753,441, filed Jan. 29, 2013.
Asseily et al., U.S. Appl. No. 12/243,718, filed Oct. 1, 2008.
Asseily et al., U.S. Appl. No. 13/431,904, filed Mar. 27, 2012.
Burnett et al., U.S. Appl. No. 13/037,057, filed Feb. 28, 2011.
L.C. Ng et al: "Denoising of Human Speech Using Combined Acoustic and EM Sensor Signal Processing", 2000 IEEE Intl Conf on Acoustics Speech and Signal Processing. Proceedings (Cat. No. OOCH37100), Istanbul, Turkey, Jun. 5-9, 2000 XP002186255, ISBN 0-7803-6293-4.
Zhao Li et al.: "Robust Speech Coding Using Microphone Arrays", Signals Systems and Computers, 1997. Conf. record of 31st Asilomar Conf, Nov. 2-5, 1997, IEEE Comput. Soc. Nov. 2, 1997, USA.
Parham Arabi, Self-Localizing Dynamic Microphone Arrays, Nov. 2002, IEEE, vol. 32 p474-485.
S. Affes et al.: "A Signal Subspace Tracking Algorithm for Microphone Array Processing of Speech". IEEE Transactions on Speech and Audio Processing, N.Y., USA vol. 5, No. 5, Sep. 1, 1997, XP000774303, ISBN 1063-6676.
Gregory C. Burnett: "The Physiological Basis of Glottal Electromagnetic Micropower Sensors (GEMS) and Their Use in Defining an Excitation Function for the Human Vocal Tract", Dissertation, University of California at Davis, Jan. 1999, USA.
A. Hussain: "Intelligibility Assessment of a Multi-Band Speech Enhancement Scheme", Proceedings IEEE Intl, Conf. on Acoustics, Speech & Signal Processing (ICASSP-2000). Istanbul, Turkey, Jun. 2000.

(56) References Cited

OTHER PUBLICATIONS

Todd J. Gable et al.: "Speaker Verification Using Combined Acoustic and EM Sensor Signal Processing", IEEE Inti. Conf. on Acoustics, Speech & Signal Processing (ICASSP-2001), Salt Lake City, USA, 2001.
Howard Weiss, USPTO Non-Final Office Action, U.S. Appl. No. 12/139,333, Mailing Date Jul. 14, 2011.
Howard Weiss, USPTO Final Office Action, U.S. Appl. No, 12/139,333, Mailing Date Apr. 10, 2012.
Shah, Paras D., USPTO Final Office Action, U.S. Appl. No. 11/805,987, Date of Mailing Nov. 16, 2009.
Shah, Paras D., USPTO Non-Final Office Action, U.S. Appl. No. 11/805,987, Date of Mailing Jan. 16, 2009.
Zhao, Eugene, USPTO Notice of References Cited, U.S. Appl. No. 12/772,963, Date of Mailing Jan. 31, 2013.
Zhao, Eugene, USPTO Non-Final Office Action, U.S. Appl. No. 12/772,963, Date of Mailing Jun. 16, 2012.
Zhao, Eugene, USPTO Notice of References Cited, U.S. Appl. No. 12/772,963, Date of Mailing Jun. 16, 2012.
ISBN: 0-8186-8316-3.
Elko et al.: "A simple adaptive first-order differential microphone", Application of Signal Processing to Audio and Acoustics, 1995., IEEE ASSP Workshop on New Paltz, NY, USA Oct. 15-18, 1995. New York, NY, USA, IEEE, US, Oct. 15, 1995, pp. 169-172, XP010154658, DOI: 10.1109/ASPAA. 1995.482983 ISBN: 978-0-7803-3064-1.
Azad, Abul, USPTO Notice of References Cited, U.S. Appl. No. 12/606,146, Date of Mailing May 17, 2012.
Monikang, George, USPTO Non-Final Office Action, U.S. Appl. No. 13/669,375, Date of Mailing Oct. 31, 2014.
Azad, Abul, USPTO Notice of References Cited, U.S. Appl. No. 12/606,140, Date of Mailing May 16, 2012.
Yogeshkurnar, Patel, USPTO Non-Final Office Action, U.S. Appl. No. 13/669,369, Date of Mailing Dec. 12, 2014.
Pham, Long, USPTO Non-Final Office Action, U.S. Appl. No. 12/772,947, Date of Mailing Nov. 6, 2012.
Le, Huyen D., USPTO Non-Final Office Action, U.S. Appl. No. 12/243,718, Mailing Date Jan. 18, 2011.
Copenheaver, Blaine R., International Searching Authority notification of transmittal of search report and written opinion of the ISA; Application No. PCT/US2011/044268, Mailing Date Nov. 25, 2011.
Jama, Isaak R. USPTO Non-Final Office Action, U.S. Appl. No. 13/184,429, Mailing Date Nov. 26, 2012.
Jama, Isaak R. USPTO Final Office Action, U.S. Appl. No. 13/184,429, Mailing Date Aug. 12, 2013.
Jama, Isaak R. USPTO Non-Final Office Action, U.S. Appl. No. 13/184,429, Mailing Date May 20, 2014.
Copenheaver, Blaine R., International Searching Authority Notification of Transmittal of Search Report and Written Opinion of the ISA, Application No. PCT/US10/40501, Mailing Date Sep. 1, 2010.
Copenheaver, Blaine R., International Searching Authority Notification of Transmittal of Search Report and Written Opinion of the ISA, Application No. PCT/US08/68634, Mailing Date Sep. 2, 2008.
Kurr, Jason R., USPTO Non-Final Office Action, U.S. Appl. No. 10/383,162, Mailing Date May 3, 2006.
Chau, Corey P. USPTO Non-Final Office Action, U.S. Appl. No. 13/301,237, Mailing Date Jun. 19, 2006.
Weiss, Howard, USPTO Final Office Action, U.S. Appl. No. 13/959,708, Mailing Date Oct. 21, 2014.
Weiss, Howard, USPTO Non-Final Office Action, U.S. Appl. No. 13/959,708, Mailing Date May 12, 2014.
Weiss, Howard, USPTO Final Office Action, U.S. Appl. No. 13/948,160, Mailing Date Oct. 14, 2014.
Weiss, Howard, USPTO Final Office Action, U.S. Appl. No. 12/139,361, Mailing Date Mar. 15, 2012.
Weiss, Howard, USPTO Non-Final Office Action, U.S. Appl. No. 12/139,361, Mailing Date Jul. 14, 2011.
Young, Lee W., International Searching Authority Notification of Transmittal of Search Report and Written Opinion of the ISA, Application No. PCT/US08/67003, Mailing Date Aug. 26, 2008.
Long, Tran, USPTO Notice a Allowance and Fee(s) Due, U.S. Appl. No. 12/163,592, Mailing Date Apr. 25, 2012.
Myrian Pierre, USPTO Non-Final Office Action, U.S. Appl. No. 09/990,847, Mailing Date Aug. 8, 2004.
Myrian Pierre, USPTO Final Office Action, U.S. Appl. No. 09/990,847, Mailing Date Jul. 7, 2005.
Holzrichter J F et al: "Speech articulator and user gesture measurements using micropower, interferometric EM-sensors" IMTC 2001. Proceedings of the 18th. IEEE Instrumentation and Measurement Technology Conference. Budapest, Hungary, May 21-23, 2001, IEEE Instrumentation and Measurement Technology Conference. (IMTC):, New York, NY: IEEE, US, vol. 1 of 3. Conf. 18, May 21, 2001, pp. 1942-1946, XP010547289 1SBN: 0-7803-6646-8.
Howard Weiss, USPTO Non-Final Office Action, U.S. Appl. No. 13/959,707, Mailing Date May 12, 2014.
Howard Weiss, USPTO Final Office Action, U.S. Appl. No. 13/959,707, Mailing Date Oct. 15, 2014.
Ammar T. Hamid, USPTO Non-Final Office Action, U.S. Appl. No. 13/431,725, Mailing Date Jul. 16, 2014.
Ammar T. Hamid, USPTO Final Office Action, U.S. Appl. No. 13/431,725, Mailing Date Dec. 23, 2014.
Xuejun Zhao, USPTO Non-Final Office Action, U.S. Appl. No. 12/772,975, Mailing Date Jun. 26, 2012.
Long Pham, USPTO Non-Final Office Action, U.S. Appl. No. 13/959,709, Mailing Date Nov. 12, 2014.
Friedrich W. Fahnert, USPTO Non-Final Office Action, U.S. Appl. No. 12/826,658, Mailing Date May 24, 2013.
Friedrich W. Fahnert, USPTO Non-Final Office Action, U.S. Appl. No. 12/826,643, Mailing Date Apr. 24, 2013.
Lun-see Lao, USPTO Non-Final Office Action, U.S. Appl. No. 12/139,344, Mailing Date Sep. 10, 2013.
Lun-see Lao, USPTO Final Office Action, U.S. Appl. No. 12/139,344, Mailing Date Aug. 27, 2012.
Lun-see Lao, USPTO Non-Final Office Action, U.S. Appl. No. 12/139,344, Mailing Date Dec. 6, 2011.
Howard Weiss, USPTO Non-Final Office Action, U.S. Appl. No. 12/139,355, Mailing Date Jul. 18, 2011.
Howard Weiss, USPTO Final Office Action, U.S. Appl. No. 12/139,355, Mailing Date Mar. 15, 2012.
Howard Weiss, USPTO Non-Final Office Action, U.S. Appl. No. 13/948,160, Mailing Date May 12, 2014.
Lee W. Young, PCT International Search Report, Application No. PCT/2008/067003, Mailing Date Aug. 26, 2008.
Lun-see Lao, USPTO Final Office Action, U.S. Appl. No. 12/163,647, Mailing Date Apr. 3, 2014.
Lun-see Lao, USPTO Non-Final Office Action, U.S. Appl. No. 12/163,647, Mailing Date Oct. 8, 2013.
Lun-see Lao, USPTO Non-Final Office Action, U.S. Appl. No. 12/163,647, Mailing Date Sep. 29, 2011.
Devona Faulk, USPTO Non-Final Office Action, U.S. Appl. No. 10/400,282, Mailing Date Aug. 14, 2012.
Devona Faulk, USPTO Non-Final Office Action, U.S. Appl. No. 10/400,282, Mailing Date Jun. 23, 2011.
Devona Faulk, USPTO Final Office Action, U.S. Appl. No. 10/400,282, Mailing Date Aug. 17, 2010.
Devona Faulk, USPTO Non-Final Office Action, U.S. Appl. No. 10/400,282, Mailing Date Dec. 9, 2009.
Devona Faulk, USPTO Non-Final Office Action, U.S. Appl. No. 10/400,282, Mailing Date Mar. 16, 2009.
Devona Faulk, USPTO Final Office Action, U.S. Appl. No. 10/400,282, Mailing Date Aug. 18, 2008.
Devona Faulk, USPTO Non-Final Office Action, U.S. Appl. No. 10/400,282, Mailing Date Oct. 30, 2007.
Devona Faulk, USPTO Non-Final Office Action, U.S. Appl. No. 10/400,282, Mailing Date Feb. 2, 2007.
Lun-See Lao, USPTO Notice of Allowance and Fees Due, U.S. Appl. No. 12/163, 675, Mailing Date Jan. 2, 2013.
Lun-See Lao, USPTO Non-Final Office Action, U.S. Appl. No. 12/163,675, Mailing Date May 17, 2012.
Long K. Tran, USPTO Non-Final Office Action, U.S. Appl. No. 13/436,765, Mailing Date Jul. 31, 2013.
L De Vos, PCT International Search Report, Application No. PCT/2003/09280, Mailing Date Sep. 16, 2003.

(56) References Cited

OTHER PUBLICATIONS

Lun-See Lao, USPTO Non-Final Office Action, U.S. Appl. No. 10/667,207, Mailing Date Dec. 24, 2009.
Lun-See Lao, USPTO Non-Final Office Action, U.S. Appl. No. 10/667,207, Mailing Date Jul. 9, 2008.
Lun-See Lao, USPTO Non-Final Office Action, U.S. Appl. No. 10/667,207, Mailing Date Feb. 9, 2007.
Lun-See Lao, USPTO Final Office Action, U.S. Appl. No. 10/667,207, Mailing Date Aug. 30, 2010.
Lun-See Lao, USPTO Final Office Action, U.S. Appl. No. 10/667,207, Mailing Date Mar. 11, 2009.
Lun-See Lao, USPTO Final Office Action, U.S. Appl. No. 10/667,207, Mailing Date Oct. 17, 2007.
Leshui Zhang, USPTO Non-Final Office Action, U.S. Appl. No. 13/037,057, Mailing Date Aug. 14, 2013.
Leshui Zhang, USPTO Final Office Action, U.S. Appl. No. 13/037,057, Mailing Date May 14, 2014.
Howard Weiss, USPTO Non-Final Office Action, U.S. Appl. No. 13/184,422, Mailing Date Oct. 18, 2013.
Xuejun Zhao, USPTO Non-Final Office Action, U.S. Appl. No. 13/753,441, Mailing Date Jul. 18, 2013.
Xuejun Zhao, USPTO Notice of Allowance and Fees Due, U.S. Appl. No. 13/753,441, Mailing Date Sep. 22, 2014.
Xuejun Zhao, USPTO Notice of Allowance and Fees Due, U.S. Appl. No. 13/753,441, Mailing Date Jan. 15, 2014.
Abul K. Azad, USPTO Final Office Action, U.S. Appl. No. 10/159,770, Mailing Date Oct. 10, 2006.
Abul K. Azad, USPTO Non-Final Office Action, U.S. Appl. No. 10/159,770, Mailing Date Dec. 15, 2005.
Paras D. Shah, USPTO Final Office Action, U.S. Appl. No. 11/805,987, Mailing Date Nov. 16, 2009.
Paras D. Shah, USPTO Non-Final Office Action, U.S. Appl. No. 11/805,987, Mailing Date Jan. 16, 2009.
Paras D. Shah, USPTO Non-Final Office Action, U.S. Appl. No. 11/805,987, Mailing Date Feb. 6, 2008.

* cited by examiner

| $n_2$ | $\Theta_{crit}$ | R | T | $T_{eff}$ |
|---|---|---|---|---|
| 1.2 | 59° | 0.006 | 0.994 | 0.65 |
| 1.3 | 68° | 0.001 | 0.999 | 0.75 |
| 1.4 | 90° | 0 | 1.0 | 1.0 |
| 1.5 | N/A | 0.001 | 0.999 | 0.99 |
| 1.6 | N/A | 0.004 | 0.096 | 0.96 |

Figure 4

| $n_2$ | $\Theta_{crit}$ | R | T | $T_{eff}$ |
|---|---|---|---|---|
| 1.0 | 46° | 0.03 | 0.97 | 0.50 |

Figure 5

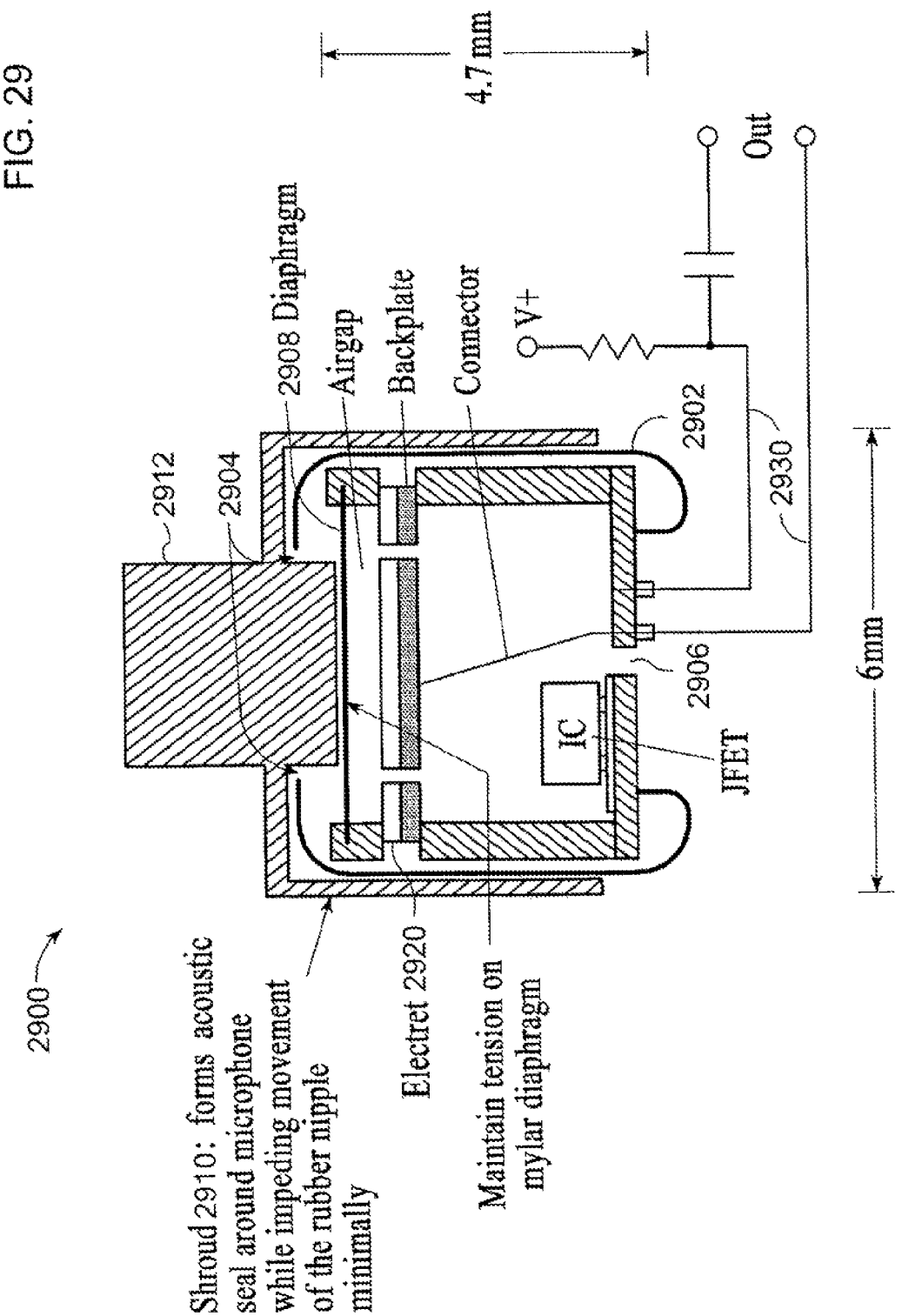

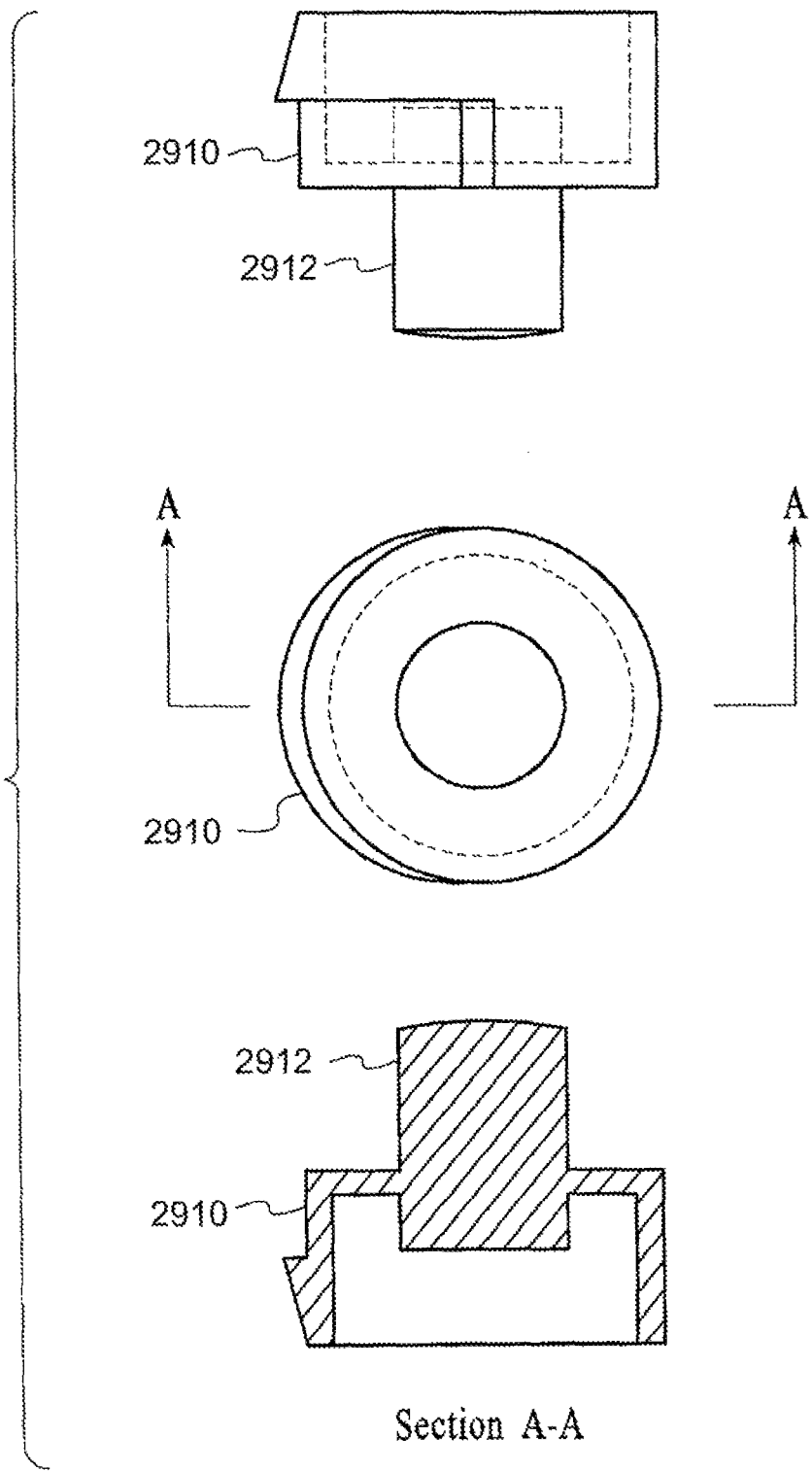

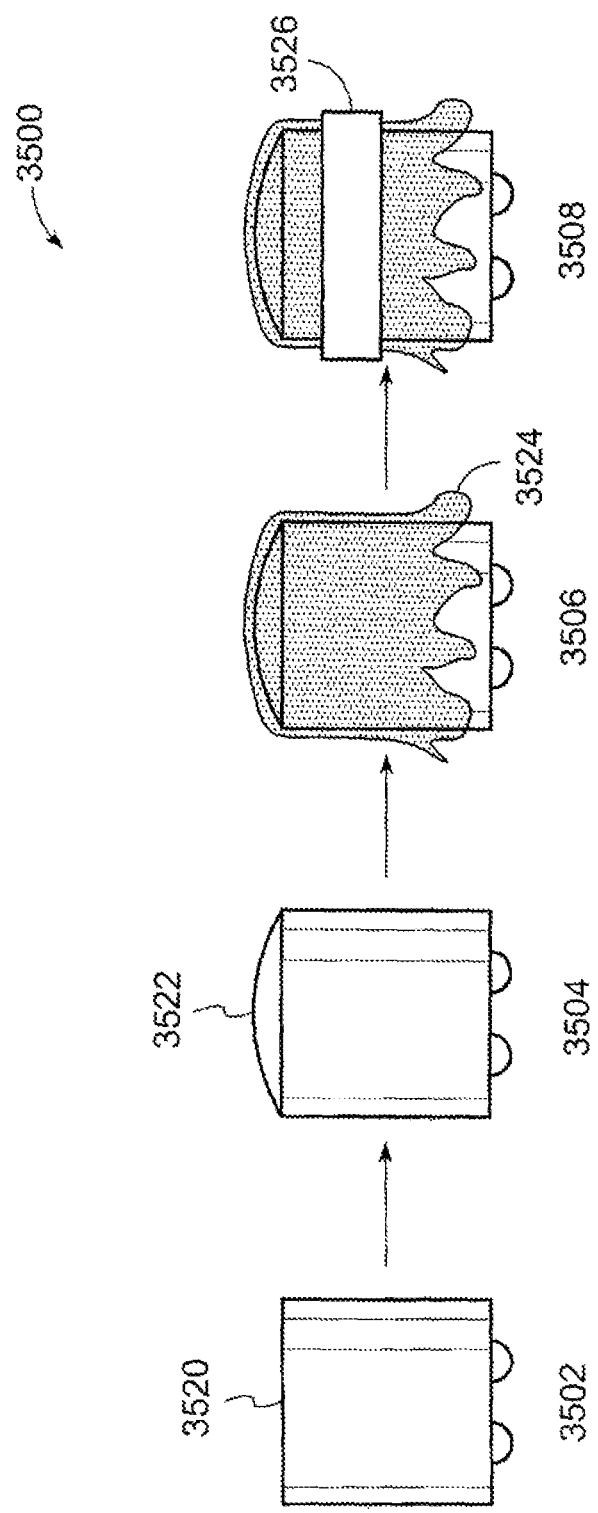

LIGHT-BASED DETECTION FOR ACOUSTIC APPLICATIONS

RELATED APPLICATIONS

This application claims the benefit of U.S. Provisional Patent Application No. 61/452,948, filed Mar. 15, 2011; and is a continuation-in-part of U.S. patent application Ser. No. 12/139,333, filed Jun. 13, 2008, which claims the benefit of U.S. Provisional Patent Application No. 60/934,551, filed Jun. 13, 2007, U.S. Provisional Patent Application No. 60/953,444, filed Aug. 1, 2007, U.S. Provisional Patent Application No. 60/954,712, filed Aug. 8, 2007, and U.S. Provisional Patent Application No. 61/045,377, filed Apr. 16, 2008; and is a continuation-in-part of U.S. patent application Ser. No. 12/243,718, filed Oct. 1, 2008, which is a continuation of U.S. patent application Ser. No. 10/769,302, filed Jan. 30, 2004, which claims the benefit of U.S. Provisional Patent Application No. 60/443,818, filed Jan. 30, 2003, all of which are herein incorporated by reference for all purposes.

FIELD

The disclosure herein relates generally to optics, communications and, more specifically, light-based detection for acoustic applications.

BACKGROUND

Skin-located vibration transducers have been in use for some time. However, conventional solutions have difficulty operating where there is inadequate or insufficient skin contact. Also, conventional solutions are not effective for directly measuring the speech of a user through his or her skin to allow the thorough removal of noise from speech without distorting the speech. Thus, what is needed is light-based detection for acoustic applications without the limitations of conventional solutions

BRIEF DESCRIPTION OF THE DRAWINGS

FIG. 4 is a table showing the effect of different user skin indices of refraction, as determined for the critical angle, R, T, and effective T (assuming random incidence angle), under an embodiment.

FIG. 5 is a table showing the variables of interest for the boot/air interface, under an embodiment.

FIG. 29 is a cross section view of an acoustic vibration sensor, under an embodiment.

FIG. 31 is a schematic diagram of a coupler of an acoustic vibration sensor, under the embodiment of FIG. 29.

FIG. 35 is a diagram of a manufacturing method for an acoustic vibration sensor, under an embodiment.

DETAILED DESCRIPTION

Figure 1:
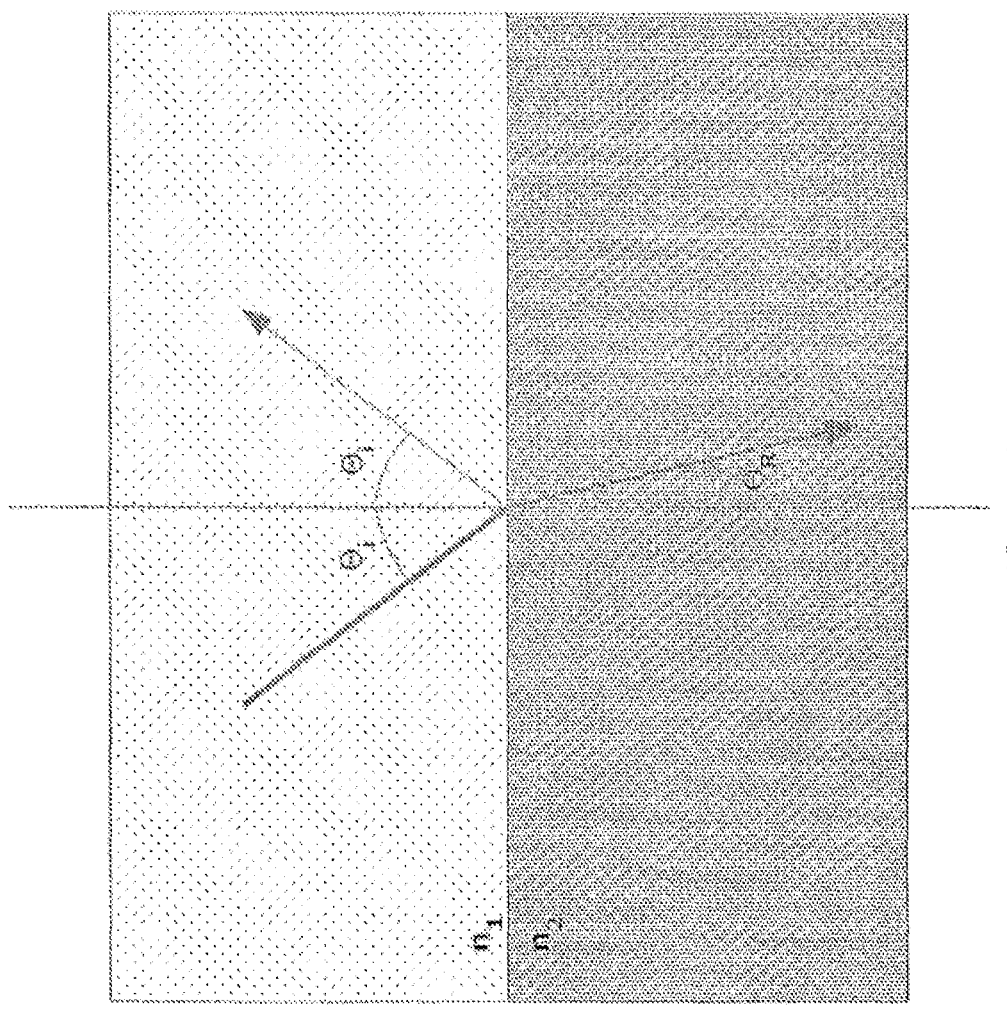
FIG. 1 depicts Snell's Law with an incident light wave reflected at the $n_1/n_2$ boundary at an angle equal to the angle of incidence, and transmitted (refracted) for certain values of $\Theta_1$ at an angle $\Theta_R$, as known in the art.

Systems and methods are described herein for detection for acoustic applications (e.g., detecting skin contact) using a gel boot. Embodiments described herein include a boot constructed so that it has an index of refraction close to (e.g., less than) the index of refraction of the user's skin at the frequency of light desired. A light emitter and detector (e.g., an infrared LED pair) are fitted into the side of the boot. Before skin contact, a significant amount of energy is reflected by the boot/air interface and the detector measures that energy. Upon skin contact, the increase or elimination of the critical angle and the closer index of reflection match of the boot/skin interface causes the amount of light energy detected by the detector to drop significantly. Digital signal processing methods are used to detect the change in light energy inside the boot.

In the following description, numerous specific details are introduced to provide a thorough understanding of, and enabling description for, embodiments. One skilled in the relevant art, however, may recognize that these embodiments can be practiced without one or more of the specific details, or with other components, systems, etc. In other instances, well-known structures or operations are not shown, or are not described in detail, to avoid obscuring aspects of the disclosed embodiments.

Unless otherwise specified, the following terms have the corresponding meanings in addition to any meaning or understanding they may convey to one skilled in the art. The term "infrared" (IR) is understood to be infrared light at a wavelength ranging from approximately 0.7 to 300 micrometers.

The vibration transducer is a very useful communication tool in both military and consumer markets. The ability to directly measure the speech of the user through his or her skin is very useful, allowing a properly configured system to thoroughly remove noise from speech without distorting the speech; such a system is available from AliphCom of San Francisco, Calif., and is described in detail herein and in U.S. patent application Ser. No. 12/139,333, which is herein incorporated by reference for all purposes.

One such transducer is the skin surface microphone (SSM), available from AliphCom of San Francisco, Calif., and described in detail herein and in U.S. patent application Ser. No. 12/243,718: which is herein incorporated by reference for all purposes. The AliphCom SSM uses a modified acoustic microphone and a flexible boot to connect the skin of the user to the interior of the microphone. The boot is generally constructed of medical-grade silicone rubber or a similar material designed for long-term, hypoallergenic contact with human skin, but is not so limited. The boot can be made to have an index of refraction close to that of human skin (e.g., approximately 1.4 for infrared light) so that light transmitted through the boot is preferentially transmitted into the skin of the user when compared to transmission from the boot to air. This difference in transmission can be detected and used to form a contact/no contact signal for use in speech detection and similar technologies.

Embodiments described herein include a method of detecting skin contact using a light-based method. More specifically, embodiments herein include a method of detecting skin contact with a gel boot (referred to herein as "the boot"). The boot of an embodiment has an index of refraction close to (e.g., less than) the index of refraction of the user's skin at the frequency of light desired. For example, the boot of an embodiment has an index of refraction less than the index of refraction of the user's skin at the frequency of light desired, but the embodiments are not so limited.

The boot of an embodiment includes a light emitter and detector housed in or fitted into the side of the boot. The light emitter and detector of an embodiment comprise an infrared light emitting diode (LED) pair, but the embodiments are not so limited. Before skin contact, a significant amount of energy is reflected by the boot/air interface and the detector measures that energy. Upon skin contact, the increase or elimination of the critical angle and the closer index of reflection match of the boot/skin interface causes the amount of light energy detected by the detector to drop significantly, and conventional digital signal processing (DSP) methods can be used to detect the change in light energy inside the boot.

Considering the theory of reflection and refraction at an interface, FIG. 1 shows the interaction of a light ray within a first substance with index of refraction $n_1$ and a second substance with an index of refraction $n_2$, as known in the art. The boundary line is considered planar, and the angle between a line perpendicular to the boundary line and the incoming ray is termed the angle of incidence and is labeled using $\Theta_i$. The corresponding line between a line perpendicular to the boundary line and the outgoing ray is called the angle of refraction and is labeled using $\Theta_R$. Snell's law states that $$\frac{\sin(\Theta_i)}{\sin(\Theta_R)} = \frac{n_2}{n_1}$$

In addition, light is reflected back into the first substance at the interface at the same angle it is incident. When traveling to an index of refraction that is less than the current index, (e.g., $n_1 > n_2$, such as from a diamond to air) the wave is completely reflected at angles of incidence greater than the critical angle, defined by $$\theta_{crit} = \sin^{-1}\left(\frac{n_2}{n_1}\right)$$

$$n_1 > n_2$$

If the angle of incidence is above the critical angle, the light ray is completely reflected at the boundary, a condition termed total internal reflection. If the angle of incidence is below the critical angle (e.g., $n_1 < n_2$, so there is no critical angle), the percentage of energy reflected at the interface is $$R = \left(\frac{n_1 - n_2}{n_1 + n_2}\right)^2$$

and the ratio of energy transmitted (T) is 1−R.

For infrared light, the index of refraction of the skin is approximately 1.4. The index of refraction of air is 1.0. Thus, to ensure maximum transmission of the light into the skin, the boot of an embodiment has an index of refraction between 1 and 1.4. If it is assumed that the boot ($n_1$) has an index of refraction of 1.4, and that the skin varies between 1.2 and 1.6, then the table of FIG. 4 shows the effect of different user skin indices of refraction, as determined for the critical angle, R, T, and effective T (assuming random incidence angle), under an embodiment.

Therefore, if the boot has an index of refraction of 1.4, and the skin index of refraction varies from 1.2 to 1.4, then the effective energy ratio transmitted at the boot/skin interface may vary between 0.65 and 1.0. This means that between 0 and 35% of the energy incident on the boot/skin interface may be reflected back into the boot. Thus it is desirable to have the index of refraction of the boot be less than that of skin ($n_1 < n_2$) so that there is no critical angle and almost all of the light energy in the boot is able to escape when it touches the skin.

Figure 5:
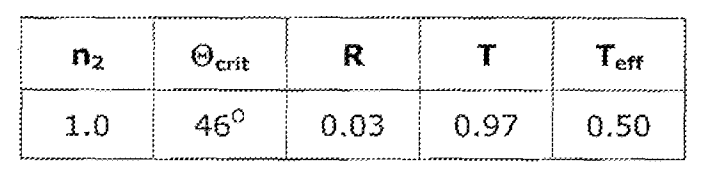

For the situation when the boot ($n_1 = 1.4$) is not against the skin of the user, $n_2 = 1.0$, the table of FIG. 5 shows the variables of interest for the boot/air interface, under an embodiment. This means that for light scattered around randomly inside the boot, about 50% of the incident light may be internally reflected at the boot/air interface. This compares to 0 to 35% of the light reflected at the boot/skin interface. Therefore, as long as the boot has an index of refraction close to or less than that of the user's skin, the change in IR energy inside the boot may be detectable and can be used to generate a contact/no contact signal.

A majority of the increase in transmission energy (and subsequent drop in energy inside the boot) is due to the increase in (for boot indices of refraction less than that of skin) or elimination of (for boot indices greater than that of skin) the critical angle. The amount of energy transmitted in either case is near 100%, so constructing the boot with an index of refraction less than that of the skin of the user may result in a larger (e.g. more easily detectable) change of energy inside the boot.

Figure 2:
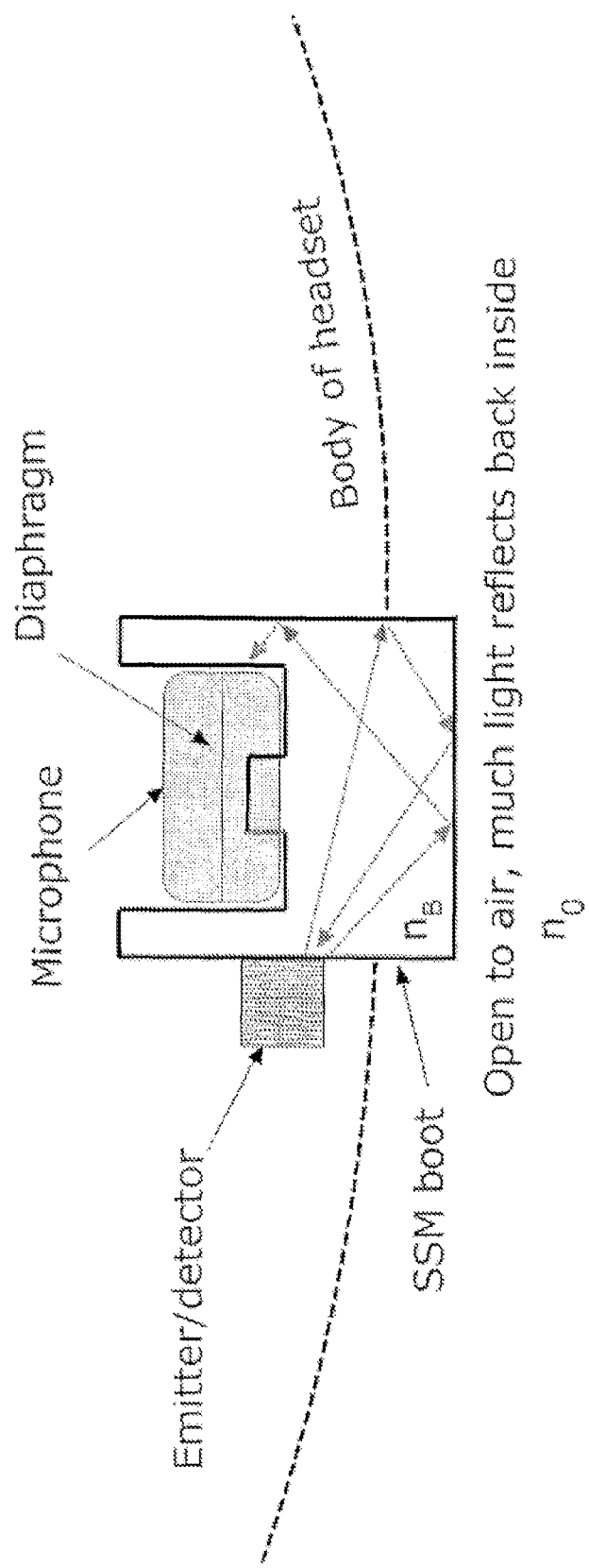
FIG. 2 shows a contact sensor open to the air so that the large difference between $n_B$ and $n_O$ means that much of the light energy is reflected back into the boot, under an embodiment.
Figure 3:
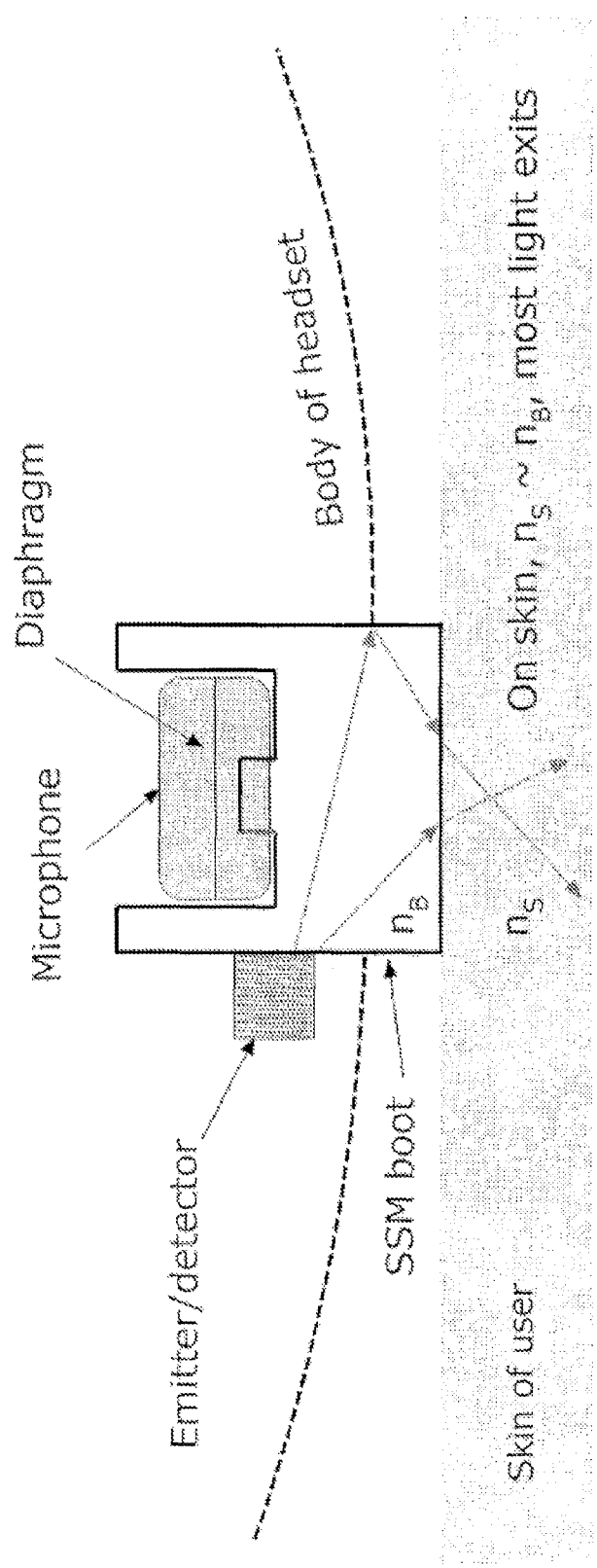
FIG. 3 shows a contact sensor adjacent or next to a user's skin such that the small difference between $n_B$ and $n_s$ increases or eliminates the critical angle and raises the transmission energy ratio so that much more energy escapes from the boot into the skin of the user, decreasing the energy in the boot, under an embodiment.

FIG. 2 and FIG. 3 show an embodiment for detecting skin contact using a light-based method, under an embodiment. FIG. 2 shows a contact sensor open to the air so that the large difference between $n_B$ and $n_0$ means that much of the light energy is reflected back into the boot, under an embodiment. FIG. 3 shows a contact sensor adjacent or next to a user's skin such that the small difference between $n_B$ and $n_s$ increases or eliminates the critical angle and raises the transmission energy ratio so that much more energy escapes from the boot into the skin of the user, decreasing the energy in the boot, under an embodiment.

The method for detecting skin contact is used in a headset, for example, the Jawbone® Icon™ available from AliphCom of San Francisco, Calif. An SSM microphone and boot are used as a vibration detector but the embodiment is not so limited. In fact, any vibration detector (including none at all) can be present as long as the embodiment uses a boot that has an index of refraction near that of skin. For example, the boot of an embodiment has an index of refraction slightly higher than the index of refraction of skin, but is not so limited.

An IR emitter/detector pair is mounted in proximity to (e.g., touching) the boot. The IR emitter/detector pair of an embodiment may be the Lite-On LTR-301 and LTR-302 (http://www.us.liteon.com/opto.index.html), but the embodiment is not so limited. While the IR emitter/detector pair is recommended for cost and availability reasons, any type of light can be used in an embodiment. Alternatively, the detector and emitter can be located on different sides of the boot; they need not be adjacent one another.

The boot of an embodiment is constructed with a moldable material that has an index of refraction approximately equal to or slightly less than the index of refraction of the skin at the frequency of the light used. For typical infrared light (e.g., 940 nm wavelength) the index of refraction of the boot should be between approximately 1.0 and 1.4. For example, the boot can be constructed using LS-3140, an optically clear encapsulation gel that has an index of refraction of approximately 1.4 and is available from NuSil (http://www.nusil.com/products/engineering/photonics/optical_gels.aspx). For best results, the emitter and detector are fitted to the boot so that they contact as much area of the boot as possible, but the embodiment is not so limited.

FIG. 2 shows an embodiment having the boot open to the air, and with a critical angle of approximately 46 degrees, under an embodiment. In this embodiment, approximately half of the light incident on the boot/air interface is reflected back inside the boot. The detector measures this energy and a signal is generated to represent this energy level.

When the boot is placed on the skin as shown in FIG. 3, the critical angle is increased or eliminated and the amount of energy transmitted at the boot/skin interface is greatly increased. This causes the amount of energy inside the boot to drop, and this decrease is reflected by the detector signal. Conventional digital signal processes (such as smoothed energy detection with a fixed threshold) are applied to detect the change in energy level inside the boot caused by the interaction of the boot and the skin. Even small gaps between the boot and the skin may be detectable using this method.

Embodiments for detecting skin contact with a gel boot described herein include a boot constructed so that it has an index of refraction close to (e.g., less than) the index of refraction of the user's skin at the frequency of light desired. A light emitter and detector (e.g., an infrared LED pair) are fitted into the side of the boot. Before skin contact, a significant amount of energy is reflected by the boot/air interface and the detector measures that energy. Upon skin contact, the increase or elimination of the critical angle and the closer index of reflection match of the boot/skin interface causes the amount of light energy detected by the detector to drop significantly. Digital signal processing methods are used to detect the change in light energy inside the boot.

A dual omnidirectional microphone array (DOMA) that provides improved noise suppression is described herein. Compared to conventional arrays and algorithms, which seek to reduce noise by nulling out noise sources, the array of an embodiment is used to form two distinct virtual directional microphones which are configured to have very similar noise responses and very dissimilar speech responses. The null formed by the DOMA is one used to remove the speech of the user from $V_2$. The two virtual microphones of an embodiment can be paired with an adaptive filter algorithm and/or VAD algorithm to significantly reduce the noise without distorting the speech, significantly improving the SNR of the desired speech over conventional noise suppression systems. The embodiments described herein are stable in operation, flexible with respect to virtual microphone pattern choice, and have proven to be robust with respect to speech source-to-array distance and orientation as well as temperature and calibration techniques.

Unless otherwise specified, the following terms have the corresponding meanings in addition to any meaning or understanding they may convey to one skilled in the art.

The term "bleedthrough" means the undesired presence of noise during speech.

The term "denoising" means removing unwanted noise from Mic1, and also refers to the amount of reduction of noise energy in a signal in decibels (dB).

The term "devoicing" means removing/distorting the desired speech from Mic1.

The term "directional microphone (DM)" means a physical directional microphone that is vented on both sides of the sensing diaphragm.

The term "Mic1 (M1)" means a general designation for an adaptive noise suppression system microphone that usually contains more speech than noise.

The term "Mic2 (M2)" means a general designation for an adaptive noise suppression system microphone that usually contains more noise than speech.

The term "noise" means unwanted environmental acoustic noise.

The term "null" means a zero or minima in the spatial response of a physical or virtual directional microphone.

The term "$O_1$" means a first physical omnidirectional microphone used to form a microphone array.

The term "$O_2$" means a second physical omnidirectional microphone used to form a microphone array.

The term "speech" means desired speech of the user.

The term "Skin Surface Microphone (SSM)" is a microphone used in an earpiece (e.g., the Jawbone® earpiece available from AliphCom of San Francisco, Calif.) to detect speech vibrations on the user's skin.

The term "$V_1$" means the virtual directional "speech" microphone, which has no nulls.

The term "$V_2$" means the virtual directional "noise" microphone, which has a null for the user's speech.

The term "Voice Activity Detection (VAD) signal" means a signal indicating when user speech is detected.

The term "virtual microphones (VM)" or "virtual directional microphones" means a microphone constructed using two or more omnidirectional microphones and associated signal processing.

Figure 6:
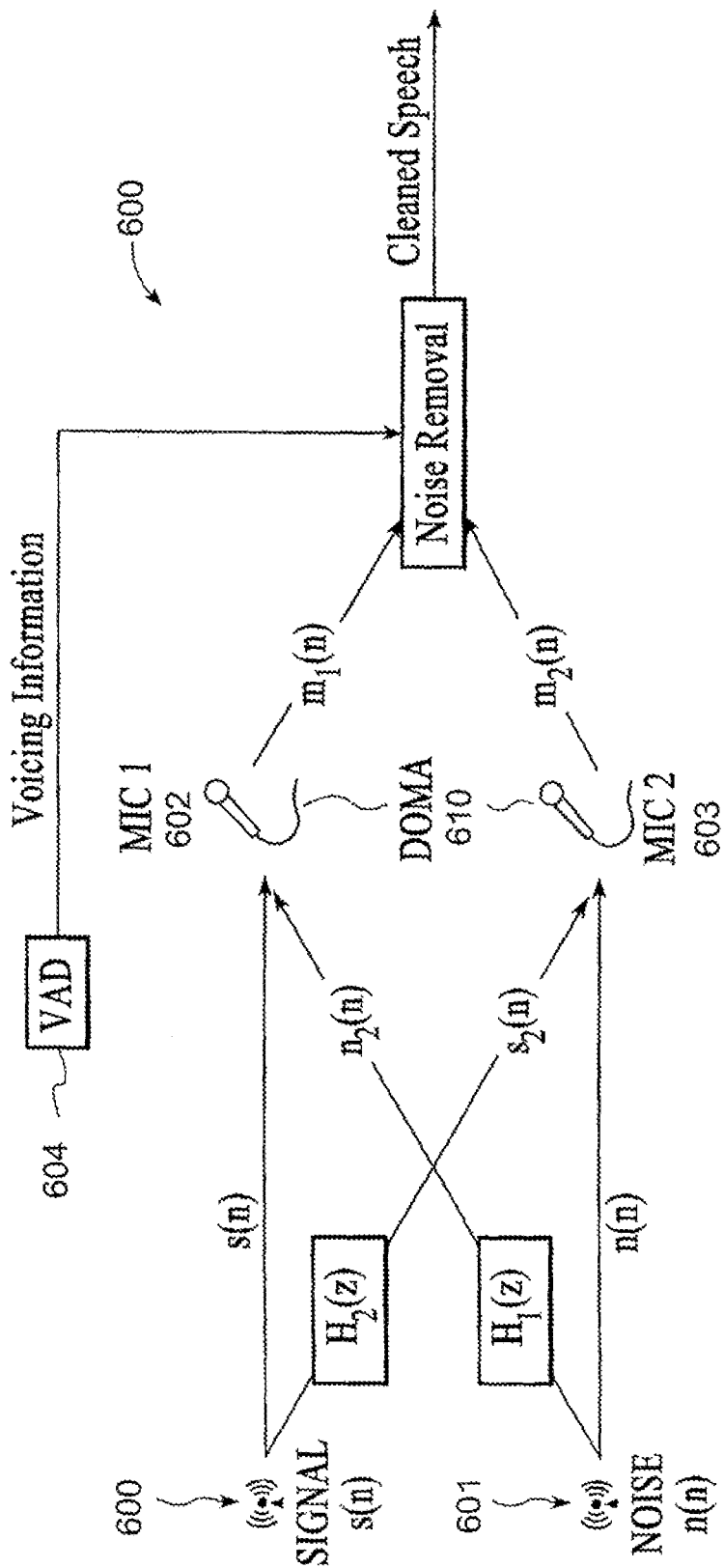
FIG. 6 is a two-microphone adaptive noise suppression system, under an embodiment.

FIG. 6 is a two-microphone adaptive noise suppression system 600, under an embodiment. The two-microphone system 600 including the combination of physical microphones MIC 1 and MIC 2 along with the processing or circuitry components to which the microphones couple (described in detail below, but not shown in this figure) is referred to herein as the dual omnidirectional microphone array (DOMA) 610, but the embodiment is not so limited. Referring to FIG. 6, in analyzing the single noise source 601 and the direct path to the microphones, the total acoustic information coming into MIC 1 (602, which can be an physical or virtual microphone) is denoted by $m_1(n)$. The total acoustic information coming into MIC 2 (603, which can also be an physical or virtual microphone) is similarly labeled $m_2(n)$. In the z (digital frequency) domain, these are represented as $M_1(z)$ and $M_2(z)$. Then, $$M_1(z)=S(z)+N_2(z)$$

$$M_2(z)=N(z)+S_2(z)$$

with $$N_2(z)=N(z)H_1(z)$$

$$S_2(z)=S(z)H_2(z),$$

so that $$M_1(z)=S(z)+N(z)H_1(z)$$

$$M_2(z)=N(z)+S(z)H_2(z). \qquad \text{Eq. 1}$$

This is the general case for all two microphone systems. Equation 1 has four unknowns and two known relationships and therefore cannot be solved explicitly.

However, there is another way to solve for some of the unknowns in Equation 1. The analysis starts with an examination of the case where the speech is not being generated, that is, where a signal from the VAD subsystem 604 (optional) equals zero. In this case, $s(n)=S(z)=0$, and Equation 1 reduces to $$M_{1N}(z)=N(z)H_1(z)$$

$$M_{2N0}(z)=N(z),$$

where the N subscript on the M variables indicate that primarily or only noise is being received. This leads to $$M_{1N}(z) = M_{2N}(z)H_1(z) \qquad \text{Eq. 2}$$

$$H_1(z) = \frac{M_{1N}(z)}{M_{2N}(z)}.$$

The function $H_1(z)$ can be calculated using any of the available system identification algorithms and the microphone outputs when the system is certain that primarily or only noise is being received. The calculation can be done adaptively, so that the system can react to changes in the noise.

A solution is now available for $H_1(z)$, one of the unknowns in Equation 1. The final unknown, $H_2(z)$, can be determined by using the instances where speech is being produced and the VAD equals one. When this is occurring, but the recent (perhaps less than 1 second) history of the microphones indicate low levels of noise, it can be assumed that $n_s=N(z)\sim 0$. Then Equation 1 reduces to $$M_{1S}(z) = S(z)$$

$$M_{2S}(z) = S(z)H_2(z)$$

-continued which in turn leads to $$M_{2S}(z) = M_{1S}(z)H_2(z)$$

$$H_2(z) = \frac{M_{2S}(z)}{M_{1S}(z)},$$

which is the inverse of the $H_1(z)$ calculation. However, it is noted that different inputs are being used (now primarily or only the speech is occurring whereas before primarily or only the noise was occurring). While calculating $H_2(z)$; the values calculated for $H_1(z)$ are held constant (and vice versa) and it is assumed that the noise level is not high enough to cause errors in the $H_2(z)$ calculation.

After calculating $H_1(z)$ and $H_2(z)$, they are used to remove the noise from the signal. If Equation 1 is rewritten as $$S(z)=M_1(z)-N(z)H_1(z)$$

$$N(z)=M_2(z)-S(z)H_2(Z)$$

$$S(z)=M_1(z)[M_2(z)-S(z)H_2(z)]H_1(z)$$

$$S(z)[1-H_2(z)H_1(z)]=M_1(z)-M_2(z)H_1(z),$$

then N(z) may be substituted as shown to solve for S(z) as $$S(z) = \frac{M_1(z) - M_2(z)H_1(z)}{1 - H_1(z)H_2(z)}. \qquad \text{Eq. 3}$$

If the transfer functions $H_1(z)$ and $H_2(z)$ can be described with sufficient accuracy, then the noise can be completely removed and the original signal recovered. This remains true without respect to the amplitude or spectral characteristics of the noise. If there is very little or no leakage from the speech source into $M_2$, then $H_2(z) \approx 0$ and Equation 3 reduces to $$S(z) \approx M_1(z) - M_2(z)H_1(z). \qquad \text{Eq. 4}$$

Equation 4 is much simpler to implement and is very stable, assuming $H_1(z)$ is stable. However, if significant speech energy is in $M_2(z)$, devoicing can occur. In order to construct a well-performing system and use Equation 4, consideration is given to the following conditions:

R1. Availability of a perfect (or at least very good) VAD in noisy conditions

R2. Sufficiently accurate $H_1(z)$

R3. Very small (ideally zero) $H_2(z)$.

R4. During speech production, $H_1(z)$ cannot change substantially.

R5. During noise, $H_2(z)$ cannot change substantially.

Condition R1 is easy to satisfy if the SNR of the desired speech to the unwanted noise is high enough. "Enough" means different things depending on the method of VAD generation. If a VAD vibration sensor is used, as in Burnett U.S. Pat. No. 7,256,048, accurate VAD in very low SNRs (−10 dB or less) is possible. Acoustic-only methods using information from $O_1$ and $O_2$ can also return accurate VADs, but are limited to SNRs of ~3 dB or greater for adequate performance.

Condition R5 is normally simple to satisfy because for most applications the microphones may not change position with respect to the user's mouth very often or rapidly. In those applications where it may happen (such as hands-free conferencing systems) it can be satisfied by configuring Mic2 so that $H_2(z) \approx 0$.

Satisfying conditions R2, R3, and R4 are more difficult but are possible given the right combination of $V_1$ and $V_2$. Methods are examined below that have proven to be effective in satisfying the above, resulting in excellent noise suppression performance and minimal speech removal and distortion in an embodiment.

The DOMA, in various embodiments, can be used with the Pathfinder system as the adaptive filter system or noise removal. The Pathfinder system, available from AliphCom, San Francisco, Calif., is described in detail in other patents and patent applications referenced herein. Alternatively, any adaptive filter or noise removal algorithm can be used with the DOMA in one or more various alternative embodiments or configurations.

When the DOMA is used with the Pathfinder system, the Pathfinder system generally provides adaptive noise cancellation by combining the two microphone signals (e.g., Mic1, Mic2) by filtering and summing in the time domain. The adaptive filter generally uses the signal received from a first microphone of the DOMA to remove noise from the speech received from at least one other microphone of the DOMA, which relies on a slowly varying linear transfer function between the two microphones for sources of noise. Following processing of the two channels of the DOMA, an output signal is generated in which the noise content is attenuated with respect to the speech content, as described in detail below.

Figure 7:
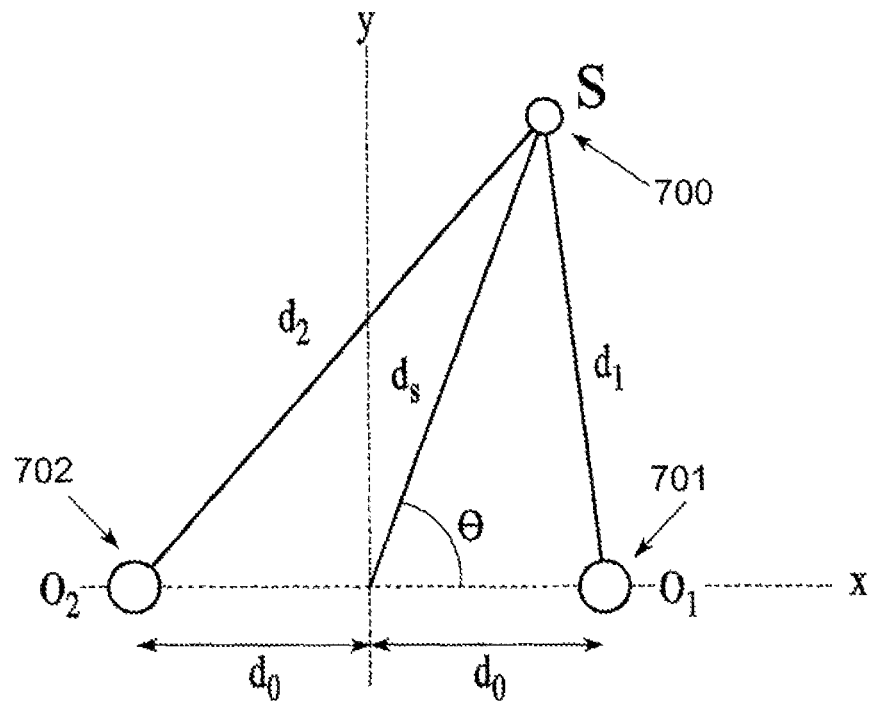
FIG. 7 is an array and speech source (S) configuration, under an embodiment. The microphones are separated by a distance approximately equal to $2d_0$, and the speech source is located a distance $d_s$ away from the midpoint of the array at an angle θ. The system is axially symmetric so only $d_s$ and θ need be specified.
Figure 8:
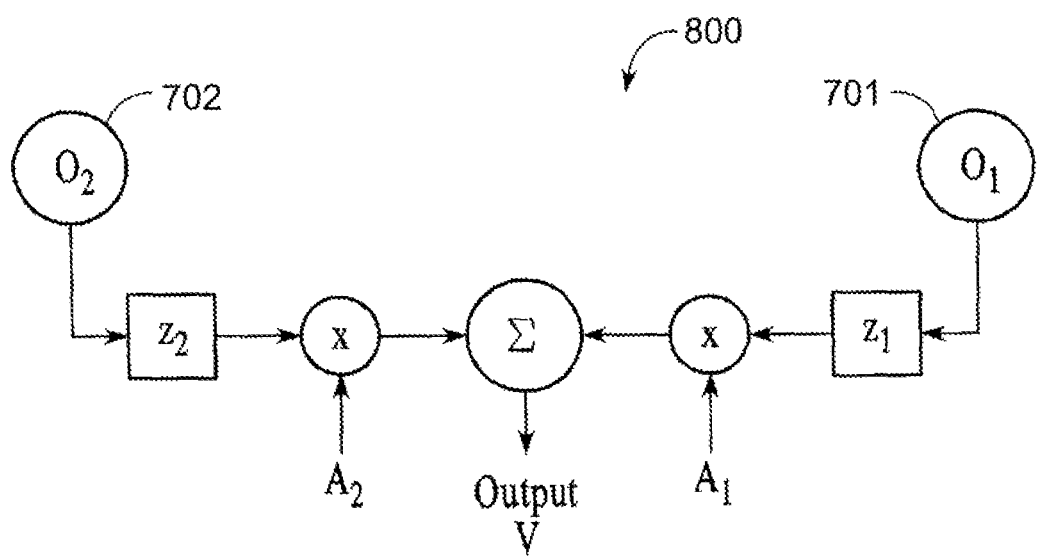
FIG. 8 is a block diagram for a first order gradient microphone using two omnidirectional elements $O_1$ and $O_2$, under an embodiment.

FIG. 7 is a generalized two-microphone array (DOMA) including an array 701/702 and speech source S configuration, under an embodiment. FIG. 8 is a system 800 for generating or producing a first order gradient microphone V using two omnidirectional elements $O_1$ and $O_2$, under an embodiment. The array of an embodiment includes two physical microphones 701 and 702 (e.g., omnidirectional microphones) placed a distance $2d_0$ apart and a speech source 700 is located a distance $d_s$ away at an angle of θ. This array is axially symmetric (at least in free space), so no other angle is needed. The output from each microphone 701 and 702 can be delayed ($z_1$ and $z_2$), multiplied by a gain ($A_1$ and $A_2$), and then summed with the other as demonstrated in FIG. 8. The output of the array is or forms at least one virtual microphone, as described in detail below. This operation can be over any frequency range desired. By varying the magnitude and sign of the delays and gains, a wide variety of virtual microphones (VMs), also referred to herein as virtual directional microphones, can be realized. There are other methods known to those skilled in the art for constructing VMs but this is a common one and may be used in the enablement below.

Figure 9:
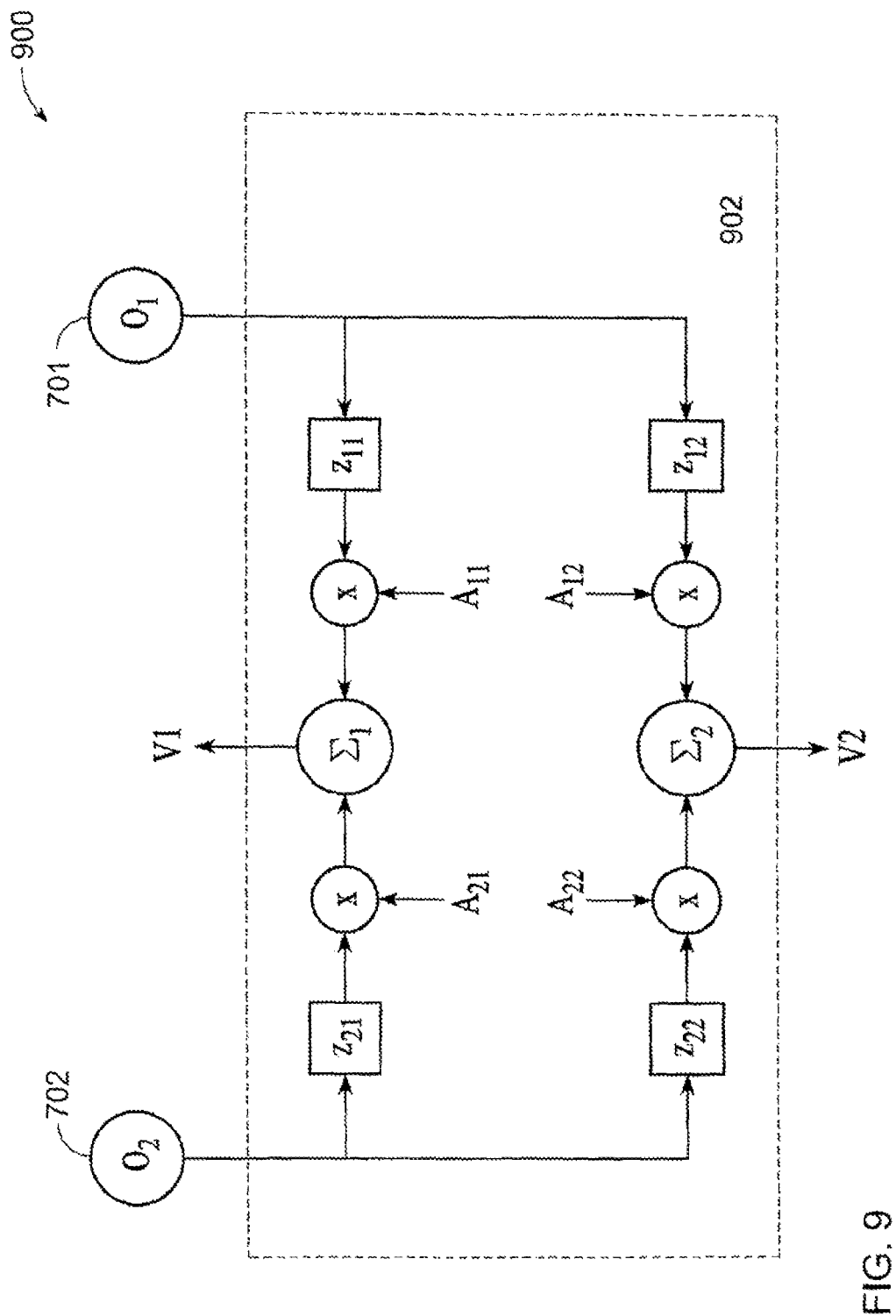
FIG. 9 is a block diagram for a DOMA including two physical microphones configured to form two virtual microphones $V_1$ and $V_2$, under an embodiment.

As an example, FIG. 9 is a block diagram for a DOMA 900 including two physical microphones configured to form two virtual microphones $V_1$ and $V_2$, under an embodiment. The DOMA includes two first order gradient microphones $V_1$ and $V_2$ formed using the outputs of two microphones or elements $O_1$ and $O_2$ (701 and 702), under an embodiment. The DOMA of an embodiment includes two physical microphones 701 and 702 that are omnidirectional microphones, as described above with reference to FIGS. 7 and 8. The output from each microphone is coupled to a processing component 902, or circuitry, and the processing component outputs signals representing or corresponding to the virtual microphones $V_1$ and $V_2$.

In this example system 900, the output of physical microphone 701 is coupled to processing component 902 that includes a first processing path that includes application of a first delay $z_{11}$ and a first gain $A_{11}$ and a second processing path that includes application of a second delay $z_{12}$ and a second gain $A_{12}$. The output of physical microphone 702 is coupled to a third processing path of the processing component 902 that includes application of a third delay $z_{21}$ and a third gain $A_{21}$ and a fourth processing path that includes application of a fourth delay $z_{22}$ and a fourth gain $A_{22}$. The output of the first and third processing paths is summed to form virtual microphone $V_1$, and the output of the second and fourth processing paths is summed to form virtual microphone $V_2$.

Figure 10:
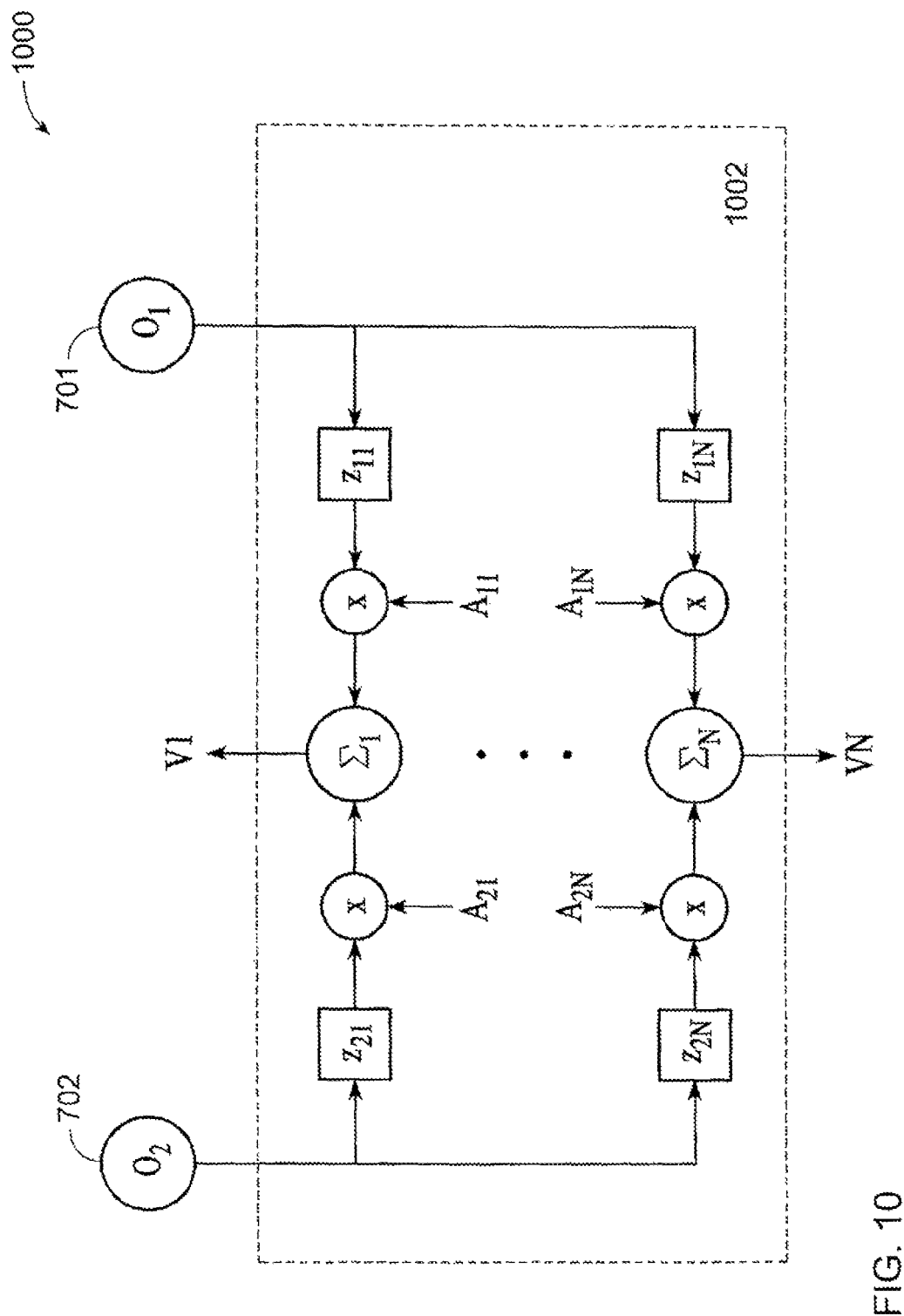
FIG. 10 is a block diagram for a DOMA including two physical microphones configured to form N virtual microphones $V_1$ through $V_N$, where N is any number greater than one, under an embodiment.

As described in detail below, varying the magnitude and sign of the delays and gains of the processing paths leads to a wide variety of virtual microphones (VMs), also referred to herein as virtual directional microphones, can be realized. While the processing component 902 described in this example includes four processing paths generating two virtual microphones or microphone signals, the embodiment is not so limited. For example, FIG. 10 is a block diagram for a DOMA 1000 including two physical microphones configured to form N virtual microphones $V_1$ through $V_N$, where N is any number greater than one, under an embodiment. Thus, the DOMA can include a processing component 1002 having any number of processing paths as appropriate to form a number N of virtual microphones.

The DOMA of an embodiment can be coupled or connected to one or more remote devices. In a system configuration, the DOMA outputs signals to the remote devices. The remote devices include, but are not limited to, at least one of cellular telephones, satellite telephones, portable telephones, wireline telephones, Internet telephones, wireless transceivers, wireless communication radios, personal digital assistants (PDAs), personal computers (PCs), headset devices, head-worn devices, and earpieces.

Furthermore, the DOMA of an embodiment can be a component or subsystem integrated with a host device. In this system configuration, the DOMA outputs signals to components or subsystems of the host device. The host device includes, but is not limited to, at least one of cellular telephones, satellite telephones, portable telephones, wireline telephones, Internet telephones, wireless transceivers, wireless communication radios, personal digital assistants (PDAs), personal computers (PCs), headset devices, head-worn devices, and earpieces.

Figure 11:
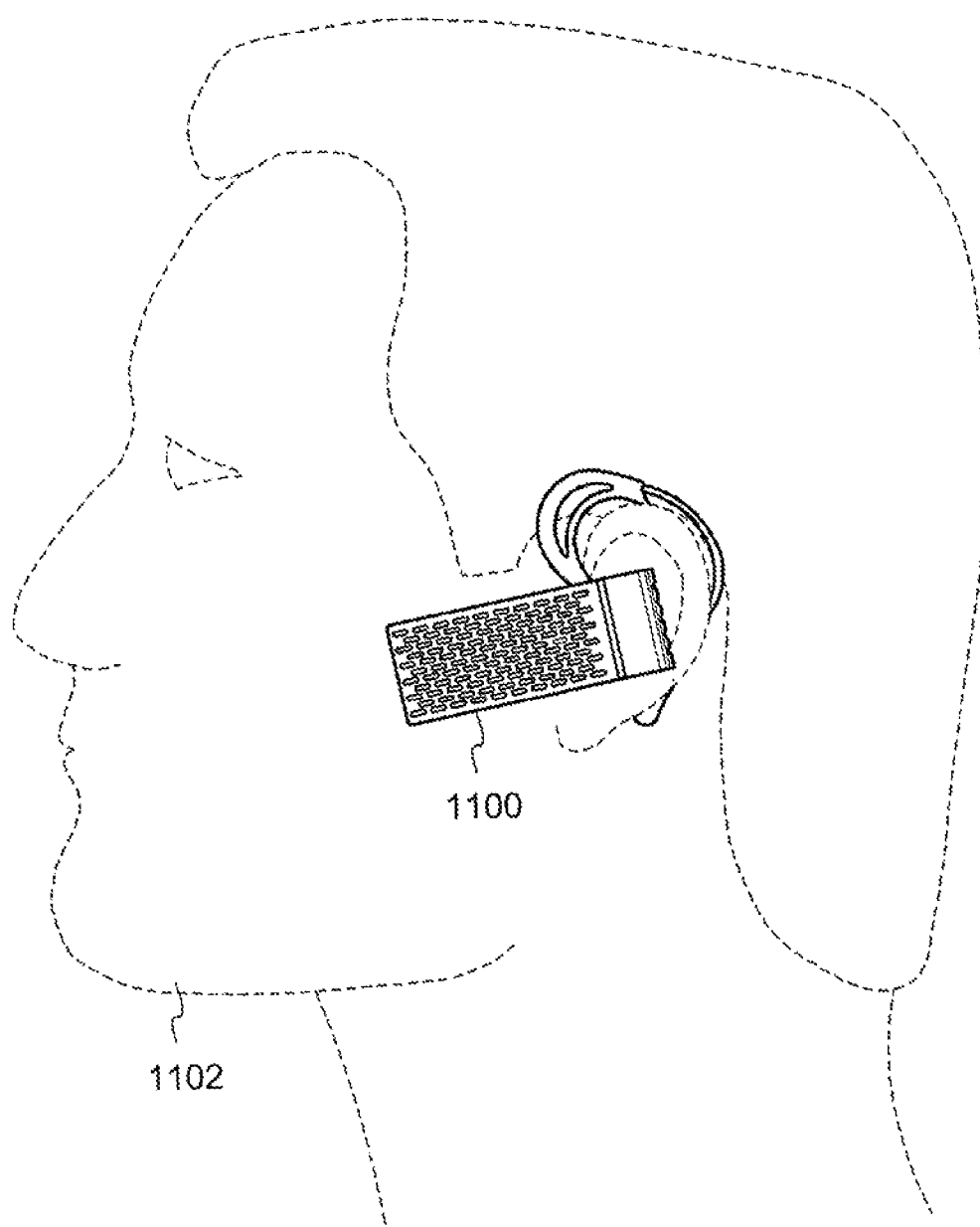
FIG. 11 is an example of a headset or head-worn device that includes the DOMA, as described herein, under an embodiment.

As an example, FIG. 11 is an example of a headset or head-worn device 1100 that includes the DOMA, as described herein, under an embodiment. The headset 1100 of an embodiment includes a housing having two areas or receptacles (not shown) that receive and hold two microphones (e.g., $O_1$ and $O_2$). The headset 1100 is generally a device that can be worn by a speaker 1102, for example, a headset or earpiece that positions or holds the microphones in the vicinity of the speaker's mouth. The headset 1100 of an embodiment places a first physical microphone (e.g., physical microphone $O_1$) in a vicinity of a speaker's lips. A second physical microphone (e.g., physical microphone $O_2$) is placed a distance behind the first physical microphone. The distance of an embodiment is in a range of a few centimeters behind the first physical microphone or as described herein (e.g., described with reference to FIGS. 6-10). The DOMA is symmetric and is used in the same configuration or manner as a single close-talk microphone, but is not so limited.

Figure 12:
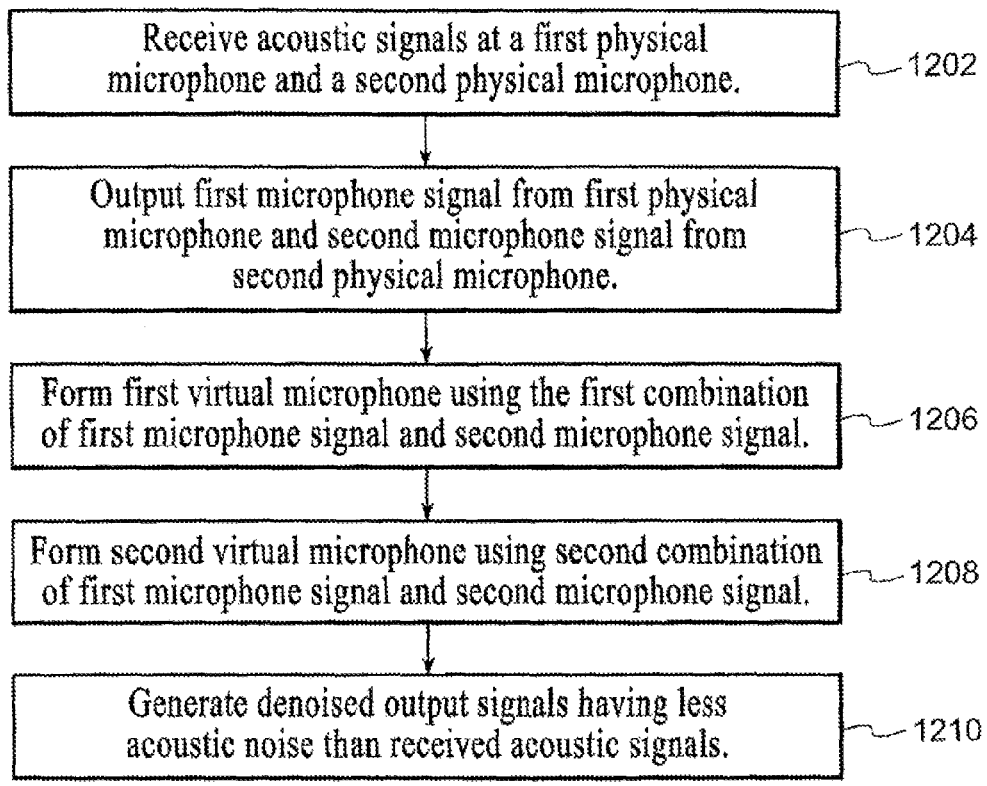
FIG. 12 is a flow diagram for denoising acoustic signals using the DOMA, under an embodiment.

FIG. 12 is a flow diagram for denoising 1200 acoustic signals using the DOMA, under an embodiment. The denoising 1200 begins by receiving 1202 acoustic signals at a first physical microphone and a second physical microphone. In response to the acoustic signals, a first microphone signal is output from the first physical microphone and a second microphone signal is output from the second physical microphone 1204. A first virtual microphone is formed 1206 by generating a first combination of the first microphone signal and the second microphone signal. A second virtual microphone is formed 1208 by generating a second combination of the first microphone signal and the second microphone signal, and the second combination is different from the first combination. The first virtual microphone and the second virtual microphone are distinct virtual directional microphones with substantially similar responses to noise and substantially dissimilar responses to speech. The denoising 1200 generates 1210 output signals by combining signals from the first virtual microphone and the second virtual microphone, and the output signals include less acoustic noise than the acoustic signals.

Figure 13:
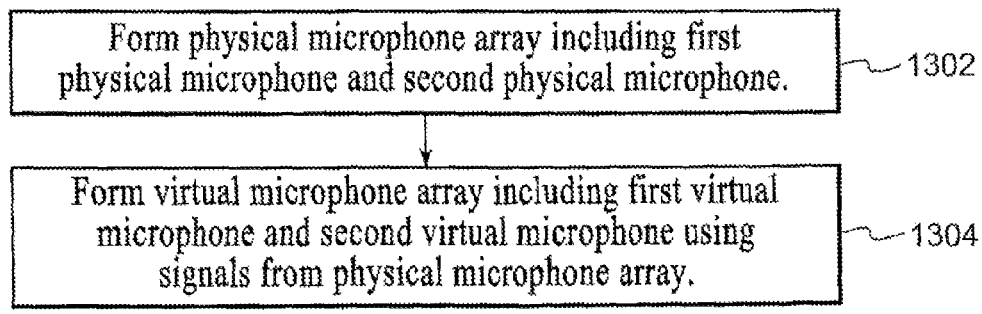
FIG. 13 is a flow diagram for forming the DOMA, under an embodiment.

FIG. 13 is a flow diagram for forming 1300 the DOMA, under an embodiment. Formation 1300 of the DOMA includes forming 1302 a physical microphone array including a first physical microphone and a second physical microphone. The first physical microphone outputs a first microphone signal and the second physical microphone outputs a second microphone signal. A virtual microphone array is formed 1304 comprising a first virtual microphone and a second virtual microphone. The first virtual microphone comprises a first combination of the first microphone signal and the second microphone signal. The second virtual microphone comprises a second combination of the first microphone signal and the second microphone signal, and the second combination is different from the first combination. The virtual microphone array including a single null oriented in a direction toward a source of speech of a human speaker.

The construction of VMs for the adaptive noise suppression system of an embodiment includes substantially similar noise response in $V_1$ and $V_2$. Substantially similar noise response as used herein means that $H_1(z)$ is simple to model and may not change much during speech, satisfying conditions R2 and R4 described above and allowing strong denoising and minimized bleedthrough.

The construction of VMs for the adaptive noise suppression system of an embodiment includes relatively small speech response for $V_2$. The relatively small speech response for $V_2$ means that $H_2(z) \approx 0$, which may satisfy conditions R3 and R5 described above.

The construction of VMs for the adaptive noise suppression system of an embodiment further includes sufficient speech response for $V_1$ so that the cleaned speech may have significantly higher SNR than the original speech captured by $O_1$.

The description that follows assumes that the responses of the omnidirectional microphones $O_1$ and $O_2$ to an identical acoustic source have been normalized so that they have exactly the same response (amplitude and phase) to that source. This can be accomplished using standard microphone array methods (such as frequency-based calibration) well known to those versed in the art.

Referring to the condition that construction of VMs for the adaptive noise suppression system of an embodiment includes relatively small speech response for $V_2$, it is seen that for discrete systems $V_2(z)$ can be represented as:

$$V_2(z) = O_2(z) - z^{-\gamma} \beta O_1(z)$$

where $$\beta = \frac{d_1}{d_2}$$

$$\gamma = \frac{d_2 - d_1}{c} \cdot f_s \text{ (samples)}$$

-continued $$d_1 = \sqrt{d_s^2 - 2d_s\cos(\theta) + d_0^2}$$

$$d_2 = \sqrt{d_s^2 - 2d_s\cos(\theta) + d_0^2}$$

The distances $d_1$ and $d_2$ are the distance from $O_1$ and $O_2$ to the speech source (see FIG. 7), respectively, and γ is their difference divided by c, the speed of sound, and multiplied by the sampling frequency $f_s$. Thus, γ is in samples, but need not be an integer. For non-integer γ, fractional-delay filters (well known to those versed in the art) may be used.

It is important to note that the β above is not the conventional β used to denote the mixing of VMs in adaptive beamforming; it is a physical variable of the system that depends on the intra-microphone distance $d_0$ (which is fixed) and the distance $d_s$ and angle θ, which can vary. As shown below, for properly calibrated microphones, it is not necessary for the system to be programmed with the exact β of the array. Errors of approximately 10-15% in the actual β (i.e. the β used by the algorithm is not the β of the physical array) have been used with very little degradation in quality. The algorithmic value of β may be calculated and set for a particular user or may be calculated adaptively during speech production when little or no noise is present. However, adaptation during use is not required for nominal performance.

Figure 14:
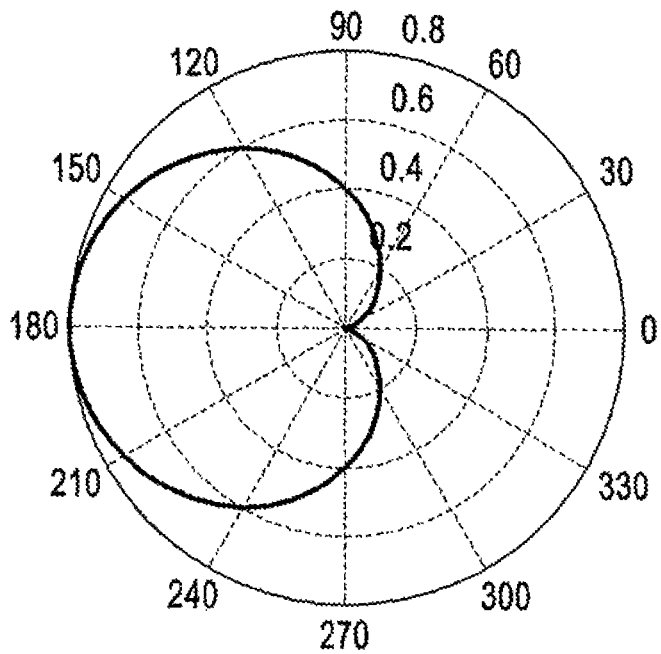
FIG. 14 is a plot of linear response of virtual microphone $V_2$ to a 1 kHz speech source at a distance of 0.1 m, under an embodiment. The null is at 0 degrees, where the speech is normally located.
Figure 15:
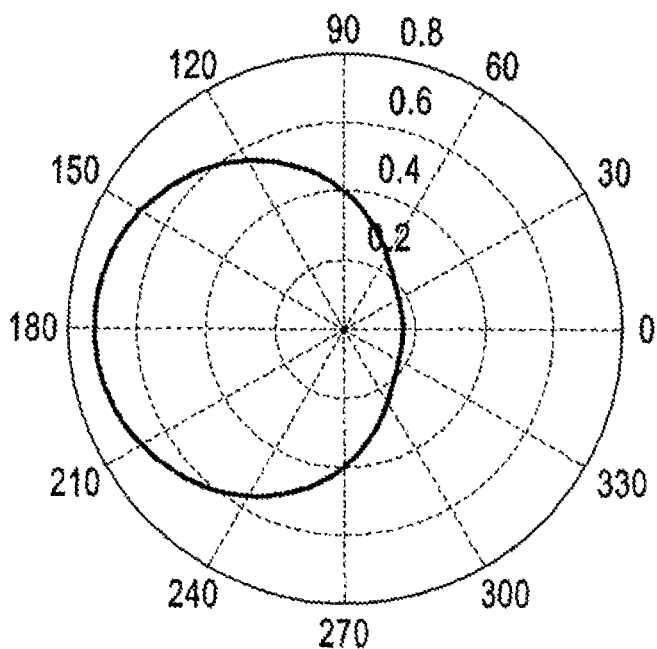
FIG. 15 is a plot of linear response of virtual microphone $V_2$ to a 1 kHz noise source at a distance of 1.0 m, under an embodiment. There is no null and all noise sources are detected.

FIG. 14 is a plot of linear response of virtual microphone $V_2$ with β=0.8 to a 1 kHz speech source at a distance of 0.1 m, under an embodiment. The null in the linear response of virtual microphone $V_2$ to speech is located at 0 degrees, where the speech is typically expected to be located. FIG. 15 is a plot of linear response of virtual microphone $V_2$ with β=0.8 to a 1 kHz noise source at a distance of 1.0 m, under an embodiment. The linear response of $V_2$ to noise is devoid of or includes no null, meaning all noise sources are detected.

The above formulation for $V_2(z)$ has a null at the speech location and may therefore exhibit minimal response to the speech. This is shown in FIG. 14 for an array with $d_0$=10.7 mm and a speech source on the axis of the array (θ=0) at 10 cm (β=0.8). Note that the speech null at zero degrees is not present for noise in the far field for the same microphone, as shown in FIG. 15 with a noise source distance of approximately 1 meter. This allows the noise in front of the user to be detected so that it can be removed. This differs from conventional systems that can have difficulty removing noise in the direction of the mouth of the user.

The $V_1(z)$ can be formulated using the general form for $V_1(z)$:

$$V_1(z) = \alpha_A O_1(z) \cdot z^{-d_A} - \alpha_B O_2(z) \cdot z^{-d_B}$$

Since $$V_2(z) = O_2(z) - z^{-\gamma}\beta O_1(z)$$

and, since for noise in the forward direction $$O_{2N}(z) = O_{1N}(z) \cdot z^{-\gamma},$$

then $$V_{2N}(z) = O_{1N}(z) \cdot z^{-\gamma} - z^{-\gamma}\beta O_{1N}(z)$$

$$V_{2N}(z) = (1-\beta)(O_{1N}(z) \cdot z^{-\gamma})$$

If this is then set to equal to $V_1(z)$ above, the result is $$V_{1N}(z) = \alpha_A O_{1N}(z) \cdot z^{-d_A} - \alpha_B O_{1N}(z) \cdot z^{-\gamma} \cdot z^{-d_B} = (1-\beta)(O_{1N}(z) \cdot z^{-\gamma})$$

thus we may set $d_A=\gamma$ $d_B=0$ $\alpha_A=1$ $\alpha_A=\beta$ to get $$V_1(z) = O_1(z) \cdot z^{-\gamma} - \beta O_2(z)$$

The definitions for $V_1$ and $V_2$ above mean that for noise $H_1(z)$ is:

$$H_1(z) = \frac{V_1(z)}{V_2(z)} = \frac{-\beta O_2(z) + O_1(z) \cdot z^{-\gamma}}{O_2(z) - z^{-\gamma}\beta O_1(z)}$$

which, if the amplitude noise responses are about the same, has the form of an allpass filter. This has the advantage of being easily and accurately modeled, especially in magnitude response, satisfying R2.

This formulation allows the noise response to be as similar as possible and the speech response to be proportional to $(1-\beta^2)$. Since β is the ratio of the distances from $O_1$ and $O_2$ to the speech source, it is affected by the size of the array and the distance from the array to the speech source.

Figure 16:
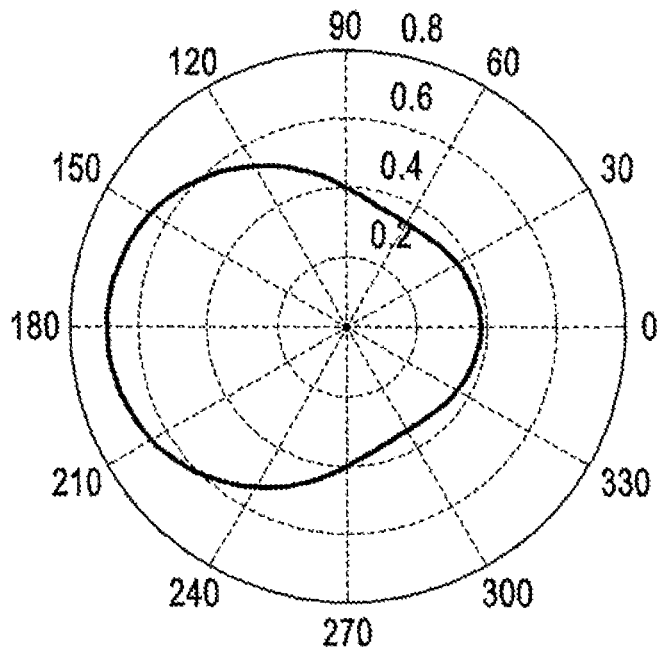
FIG. 16 is a plot of linear response of virtual microphone $V_1$ to a 1 kHz speech source at a distance of 0.1 m, under an embodiment. There is no null and the response for speech is greater than that shown in FIG. 19.

FIG. 16 is a plot of linear response of virtual microphone $V_1$ with β=0.8 to a 1 kHz speech source at a distance of 0.1 m, under an embodiment. The linear response of virtual microphone $V_1$ to speech is devoid of or includes no null and the response for speech is greater than that shown in FIG. 14.

Figure 17:
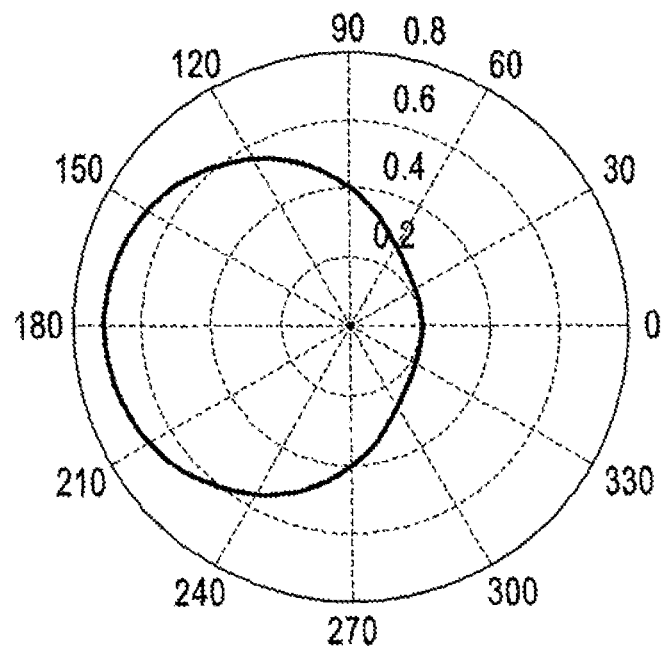
FIG. 17 is a plot of linear response of virtual microphone $V_1$ to a 1 kHz noise source at a distance of 1.0 m, under an embodiment. There is no null and the response is very similar to $V_2$ shown in FIG. 20.

FIG. 17 is a plot of linear response of virtual microphone $V_1$ with β=0.8 to a 1 kHz noise source at a distance of 1.0 m, under an embodiment. The linear response of virtual microphone $V_1$ to noise is devoid of or includes no null and the response is very similar $V_2$ shown in FIG. 15.

Figure 18:
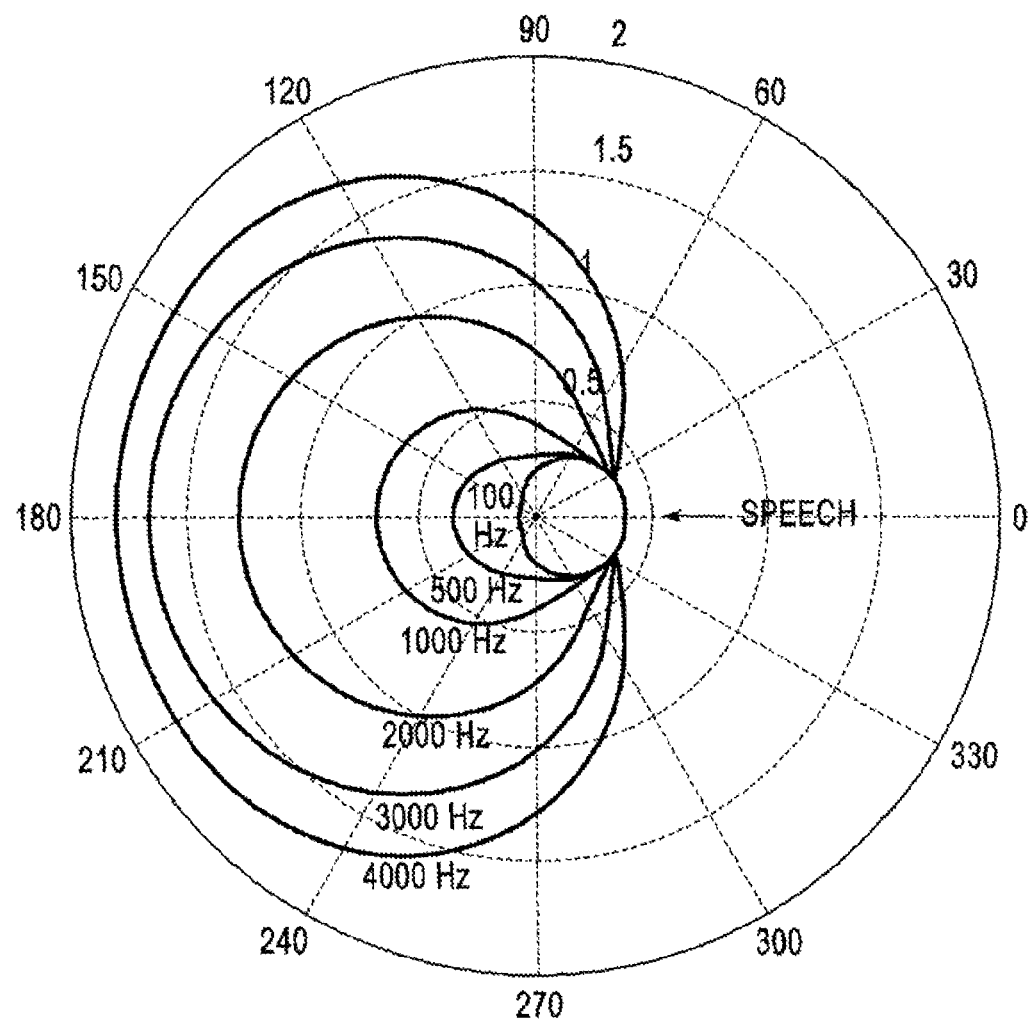
FIG. 18 is a plot of linear response of virtual microphone $V_1$ to a speech source at a distance of 0.1 m for frequencies of 100, 500, 1000, 2000, 3000, and 4000 Hz, under an embodiment.
Figure 19:
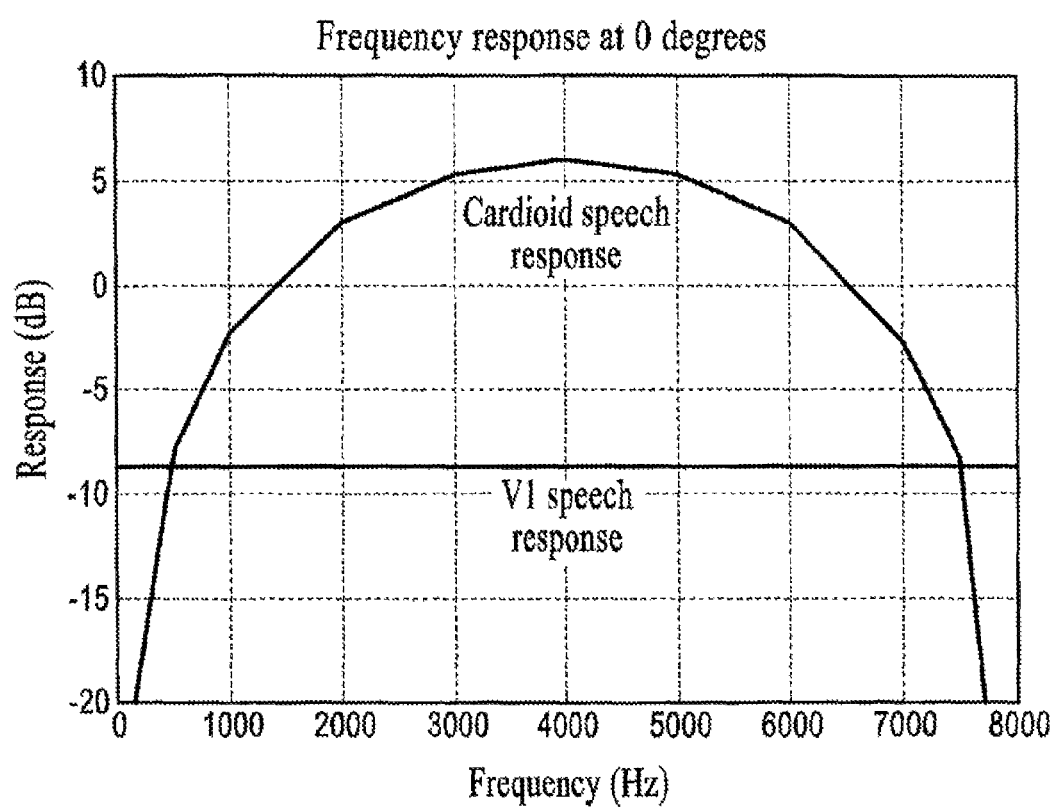
FIG. 19 is a plot showing comparison of frequency responses for speech for the array of an embodiment and for a conventional cardioids microphone.

FIG. 18 is a plot of linear response of virtual microphone $V_1$ with β=0.8 to a 1 kHz noise source at a distance of 0.1 m for frequencies of 100, 500, 1000, 2000, 3000, and 4000 Hz, under an embodiment. FIG. 19 is a plot showing comparison of frequency responses for speech for the array of an embodiment and for a conventional cardioid microphone.

The response of $V_1$ to speech is shown in FIG. 16, and the response to noise in FIG. 17. Note the difference in speech response compared to $V_2$ shown in FIG. 14 and the similarity of noise response shown in FIG. 15. Also note that the orientation of the speech response for $V_1$ shown in FIG. 16 is completely opposite the orientation of conventional systems, where the main lobe of response is normally oriented toward the speech source. The orientation of an embodiment, in which the main lobe of the speech response of $V_1$ is oriented away from the speech source, means that the speech sensitivity of $V_1$ is lower than a normal directional microphone but is flat for all frequencies within approximately +−30 degrees of the axis of the array, as shown in FIG. 18. This flatness of response for speech means that no shaping postfilter is needed to restore omnidirectional frequency response. This does come at a price—as shown in FIG. 19, which shows the speech response of $V_1$ with β=0.8 and the speech response of a cardioid microphone. The speech response of $V_1$ is approximately 0 to ~13 dB less than a normal directional microphone between approximately 500 and 7500 Hz and approximately 0 to 10+ dB greater than a directional microphone below approximately 500 Hz and above 7500 Hz for a sampling frequency of approximately 16000 Hz. However, the superior noise suppression made possible using this system more than compensates for the initially poorer SNR.

It should be noted that FIGS. 14-17 assume the speech is located at approximately 0 degrees and approximately 10 cm, $\beta$=0.8, and the noise at all angles is located approximately 1.0 meter away from the midpoint of the array. Generally, the noise distance is not required to be 1 m or more, but the denoising is the best for those distances. For distances less than approximately 1 m, denoising may not be as effective due to the greater dissimilarity in the noise responses of $V_1$ and $V_2$. This has not proven to be an impediment in practical use—in fact, it can be seen as a feature. Any "noise" source that is ~10 cm away from the earpiece is likely to be desired to be captured and transmitted.

The speech null of $V_2$ means that the VAD signal is no longer a critical component. The VAD's purpose was to ensure that the system would not train on speech and then subsequently remove it, resulting in speech distortion. If, however, $V_2$ contains no speech, the adaptive system cannot train on the speech and cannot remove it. As a result, the system can denoise all the time without fear of devoicing, and the resulting clean audio can then be used to generate a VAD signal for use in subsequent single-channel noise suppression algorithms such as spectral subtraction. In addition, constraints on the absolute value of $H_1(z)$ (i.e. restricting it to absolute values less than two) can keep the system from fully training on speech even if it is detected. In reality, though, speech can be present due to a mis-located $V_2$ null and/or echoes or other phenomena, and a VAD sensor or other acoustic-only VAD is recommended to minimize speech distortion.

Depending on the application, $\beta$ and $\gamma$ may be fixed in the noise suppression algorithm or they can be estimated when the algorithm indicates that speech production is taking place in the presence of little or no noise. In either case, there may be an error in the estimate of the actual $\beta$ and $\gamma$ of the system. The following description examines these errors and their effect on the performance of the system. As above, "good performance" of the system indicates that there is sufficient denoising and minimal devoicing.

The effect of an incorrect $\beta$ and $\gamma$ on the response of $V_1$ and $V_2$ can be seen by examining the definitions above:

$$V_1(z) = O_1(z) \cdot z^{-\gamma T} - \beta_T O_2(z)$$

$$V_2(z) = O_2(z) \cdot z^{-\gamma T} \beta_T O_1(z)$$

where $\beta_T$ and $\gamma_T$ denote the theoretical estimates of $\beta$ and $\gamma$ used in the noise suppression algorithm. In reality, the speech response of $O_2$ is $$O_{2S}(z) = \beta_R O_{1S}(z) \cdot z^{-\gamma R}.$$

where $\beta_R \gamma_R$ denote the real $\beta$ and $\gamma$ of the physical system. The differences between the theoretical and actual values of $\beta$ and $\gamma$ can be due to mis-location of the speech source (it is not where it is assumed to be) and/or a change in the air temperature (which changes the speed of sound). Inserting the actual response of $O_2$ for speech into the above equations for $V_1$ and $V_2$ yields $$V_{1S}(z) = O_{1S}(z)[z^{-\gamma T} - \beta_T \beta_R z^{-\gamma R}]$$

$$V_{2s}(z) = O_{1S}(z)[\beta_R z^{-\gamma R} - \beta_T z^{-\gamma T}]$$

If the difference in phase is represented by $$Y_R = Y_T + Y_D$$

And the difference in amplitude as $$\beta_R = B \beta_T$$

then $$V_{1S}(z) = O_{1S}(z) z^{-\gamma T}[1 - B\beta_T^2 z^{-\gamma D}]$$

$$V_{2S}(z) = \beta_T O_{1S}(z) z^{-\gamma T}[B z^{-\gamma D} - 1]. \qquad \text{Eq. 5}$$

Figure 20:
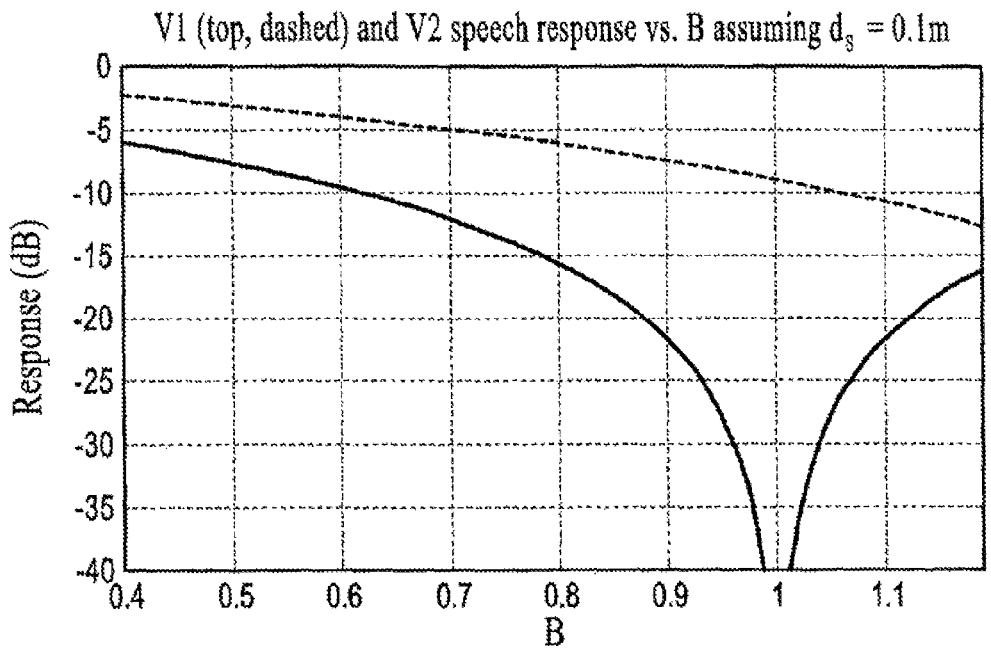
FIG. 20 is a plot showing speech response for $V_1$ (top, dashed) and $V_2$ (bottom, solid) versus B with $d_s$ assumed to be 0.1 m, under an embodiment. The spatial null in $V_2$ is relatively broad.
Figure 21:
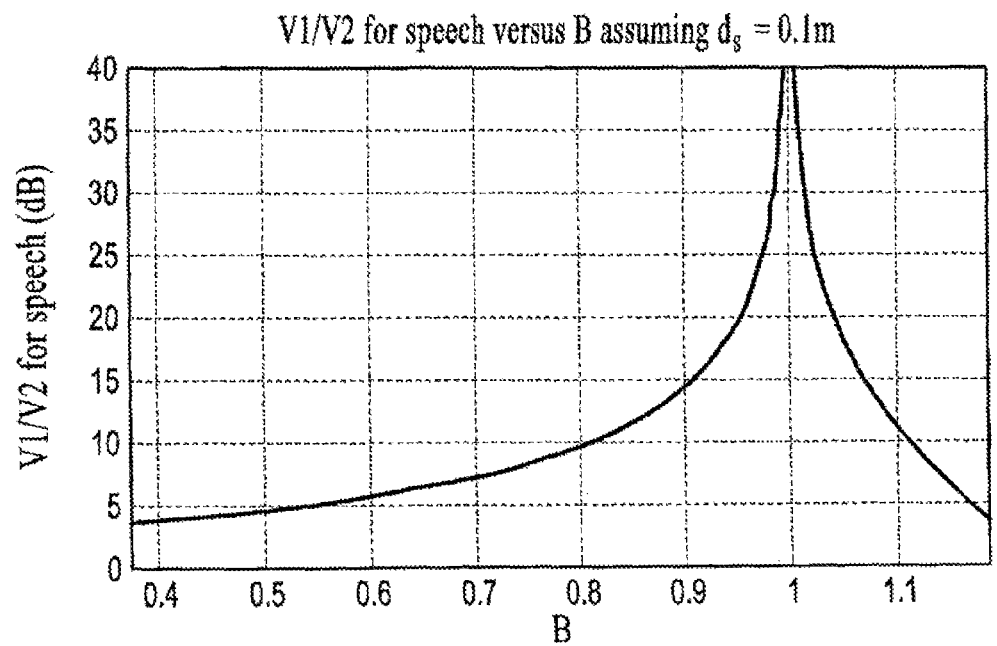
FIG. 21 is a plot showing a ratio of $V_1/V_2$ speech responses shown in FIG. 10 versus B, under an embodiment. The ratio is above 10 dB for all 0.8<B<1.1. This means that the physical β of the system need not be exactly modeled for good performance.
Figure 22:
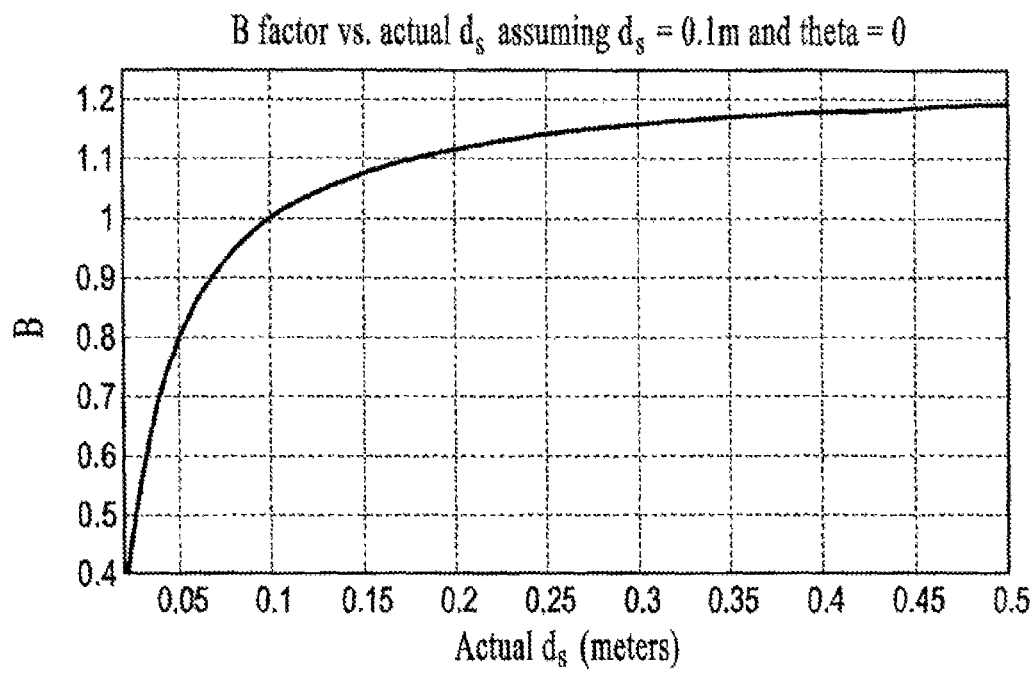
FIG. 22 is a plot of B versus actual $d_s$ assuming that $d_s$=10 cm and theta=0, under an embodiment.
Figure 23:
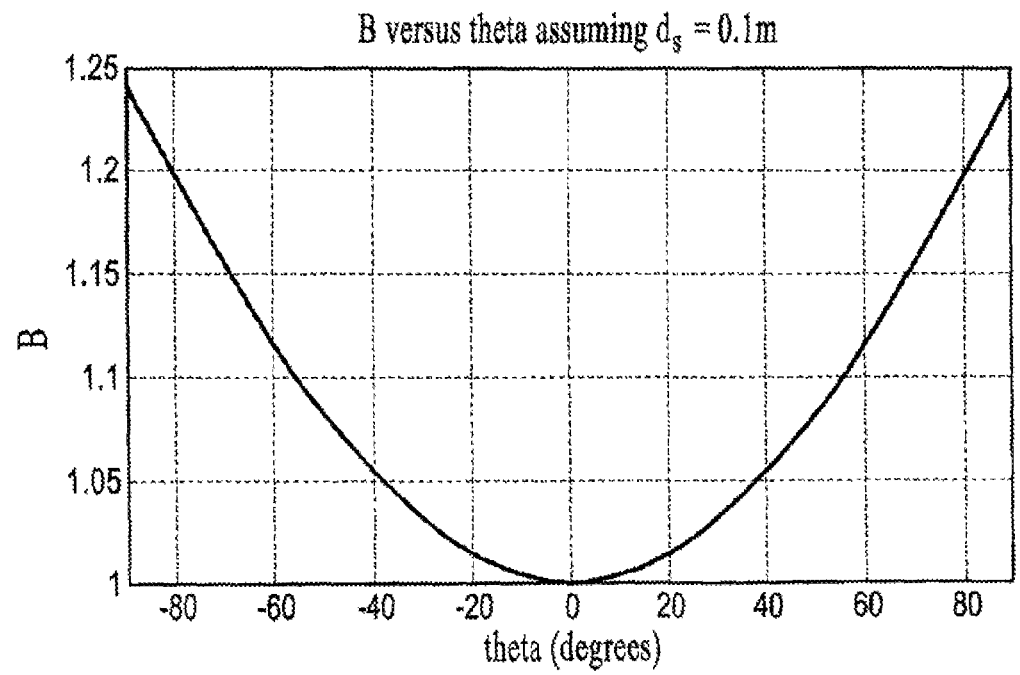
FIG. 23 is a plot of B versus theta with $d_s$=10 cm and assuming $d_s$=10 cm, under an embodiment.

The speech cancellation in $V_2$ (which directly affects the degree of devoicing) and the speech response of $V_1$ may be dependent on both B and D. An examination of the case where D=0 follows. FIG. 20 is a plot showing speech response for $V_1$ (top, dashed) and $V_2$ (bottom, solid) versus B with $d_s$ assumed to be 0.1 m, under an embodiment. This plot shows the spatial null in $V_2$ to be relatively broad. FIG. 21 is a plot showing a ratio of $V_1/V_2$ speech responses shown in FIG. 15 versus B, under an embodiment. The ratio of $V_1/V_2$ is above 10 dB for all 0.8<B<1.1, and this means that the physical $\beta$ of the system need not be exactly modeled for good performance. FIG. 22 is a plot of B versus actual $d_s$ assuming that $d_s$=10 cm and theta=0, under an embodiment. FIG. 23 is a plot of B versus theta with $d_s$=10 cm and assuming $d_s$=10 cm, under an embodiment.

In FIG. 20, the speech response for $V_1$ (upper, dashed) and $V_2$ (lower, solid) compared to $O_1$ is shown versus B when $d_s$ is thought to be approximately 10 cm and $\theta$=0. When B=1, the speech is absent from $V_2$. In FIG. 21, the ratio of the speech responses in FIG. 15 is shown. When 0.8<B<1.1, the $V_1/V_2$ ratio is above approximately 10 dB—enough for good performance. Clearly, if D=0, B can vary significantly without adversely affecting the performance of the system. Again, this assumes that calibration of the microphones so that both their amplitude and phase response is the same for an identical source has been performed.

The B factor can be non-unity for a variety of reasons. Either the distance to the speech source or the relative orientation of the array axis and the speech source or both can be different than expected. If both distance and angle mismatches are included for B, then $$B = \frac{\beta_R}{\beta_T} \frac{\sqrt{d_{SR}^2 - 2d_{SR}d_0\cos(\theta_R) + d_0^2}}{\sqrt{d_{SR}^2 + 2d_{SR}d_0\cos(\theta_R) + d_0^2}} \cdot \frac{\sqrt{d_{ST}^2 + 2d_{ST}d_0\cos(\theta_T) + d_0^2}}{\sqrt{d_{ST}^2 - 2d_{ST}d_0\cos(\theta_T) + d_0^2}}$$

where again the T subscripts indicate the theorized values and R the actual values. In FIG. 22, the factor B is plotted with respect to the actual $d_s$ with the assumption that $d_s$=10 cm and $\theta$=0. So, if the speech source in on-axis of the array, the actual distance can vary from approximately 5 cm to 18 cm without significantly affecting performance—a significant amount. Similarly, FIG. 23 shows what happens if the speech source is located at a distance of approximately 10 cm but not on the axis of the array. In this case, the angle can vary up to approximately +−55 degrees and still result in a B less than 1.1, assuring good performance. This is a significant amount of allowable angular deviation. If there is both angular and distance errors, the equation above may be used to determine if the deviations may result in adequate performance. Of course, if the value for $\beta_T$ is allowed to update during speech, essentially tracking the speech source, then B can be kept near unity for almost all configurations.

An examination follows of the case where B is unity but D is nonzero. This can happen if the speech source is not where it is thought to be or if the speed of sound is different from what it is believed to be. From Equation 5 above, it can be sees that the factor that weakens the speech null in $V_2$ for speech is $$N(z)=Bz^{-\gamma D}-1$$

or in the continuous s domain $$N(s)=Be^{-Ds}-1.$$

Figure 24:
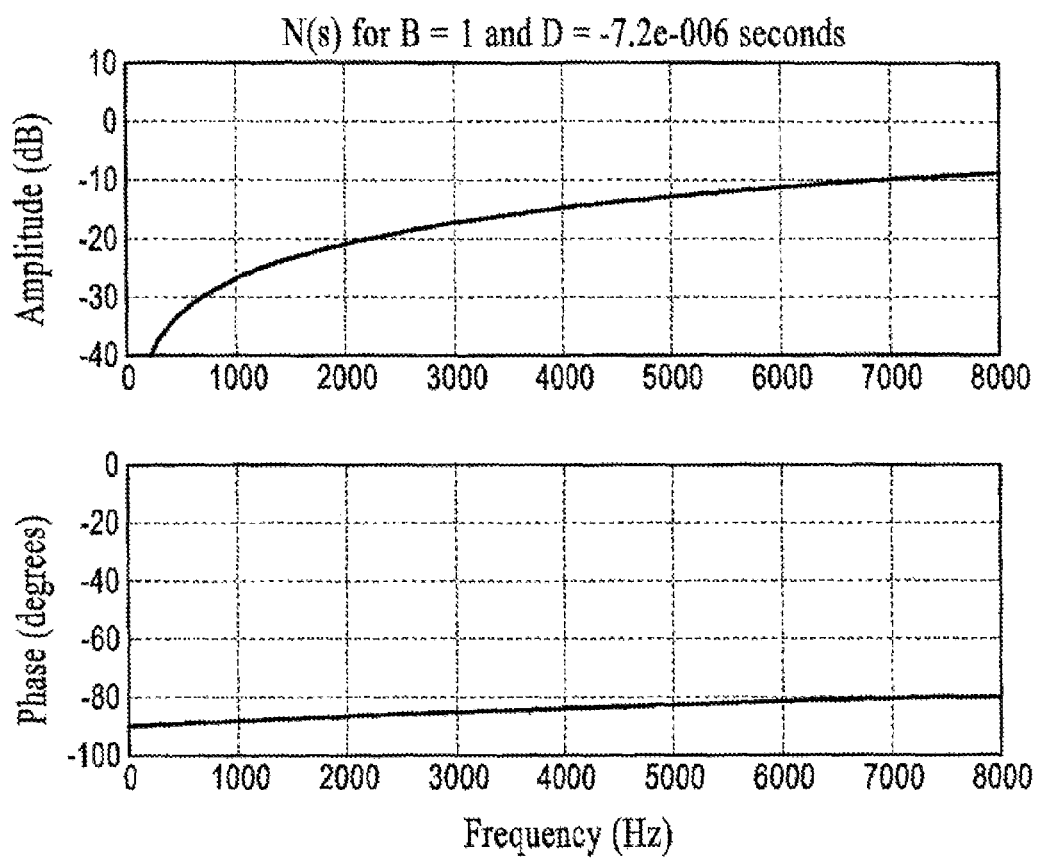
FIG. 24 is a plot of amplitude (top) and phase (bottom) response of N(s) with B=1 and D=−7.2 μsec, under an embodiment. The resulting phase difference clearly affects high frequencies more than low.

Since $\gamma$ is the time difference between arrival of speech at $V_1$ compared to $V_2$ it can be errors in estimation of the angular location of the speech source with respect to the axis of the array and/or by temperature changes. Examining the temperature sensitivity, the speed of sound varies with temperature as $$c=331.3+(0.606T)\text{m/s}$$

where T is degrees Celsius. As the temperature decreases, the speed of sound also decreases. Setting 20 C as a design temperature and a maximum expected temperature range to −40 C to +60 C (−40 F to 140 F). The design speed of sound at 20 C is 343 m/s and the slowest speed of sound may be 307 m/s at −40 C with the fastest speed of sound 362 m/s at 60 C. Set the array length ($2d_0$) to be 21 mm. For speech sources on the axis of the array, the difference in travel time for the largest change in the speed of sound is $$\nabla t_{MAX} = \frac{d}{c_1} - \frac{d}{c_2} = 0.021 \text{ m}\left(\frac{1}{343 \text{ m/s}} - \frac{1}{307 \text{ m/s}}\right) = -7.2 \times 10^{-6} \text{sec}$$

or approximately 7 microseconds. The response for N(s) given B=1 and D=7.2 μsec is shown in FIG. 24. FIG. 24 is a plot of amplitude (top) and phase (bottom) response of N(s) with B=1 and D=−7.2 μsec, under an embodiment. The resulting phase difference clearly affects high frequencies more than low. The amplitude response is less than approximately −10 dB for all frequencies less than 7 kHz and is about −9 dB at 8 kHz. Therefore, assuming B=1, this system would likely perform well at frequencies up to approximately 8 kHz. This means that a properly compensated system would work well even up to 8 kHz in an exceptionally wide (e.g., −40 C to 80 C) temperature range. Note that the phase mismatch due to the delay estimation error causes N(s) to be much larger at high frequencies compared to low.

Figure 25:
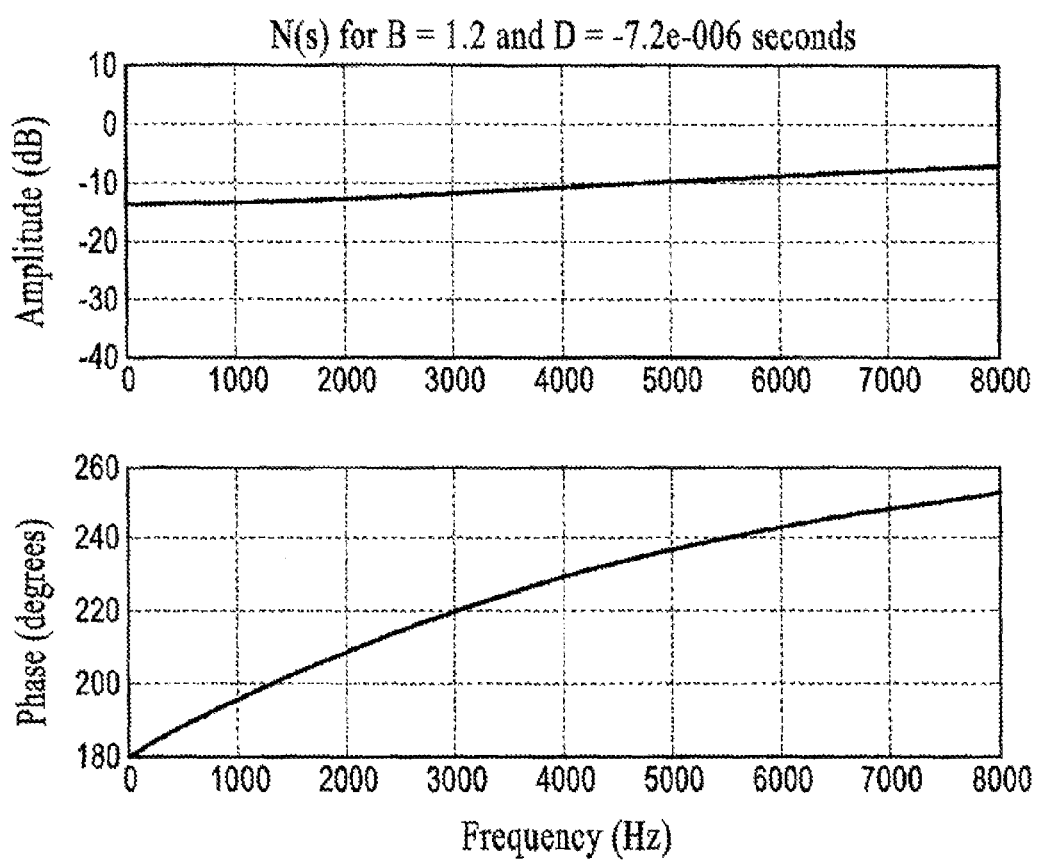
FIG. 25 is a plot of amplitude (top) and phase (bottom) response of N(s) with B=1.2 and D=−7.2 μsec, under an embodiment. Non-unity B affects the entire frequency range.

If B is not unity, the robustness of the system is reduced since the effect from non-unity B is cumulative with that of non-zero D. FIG. 25 shows the amplitude and phase response for B=1.2 and D=7.2 μsec. FIG. 25 is a plot of amplitude (top) and phase (bottom) response of N(s) with B=1.2 and D=−7.2 μsec, under an embodiment. Non-unity B affects the entire frequency range. Now N(s) is below approximately −10 dB for frequencies less than approximately 5 kHz and the response at low frequencies is much larger. Such a system would still perform well below 5 kHz and would only suffer from slightly elevated devoicing for frequencies above 5 kHz. For ultimate performance, a temperature sensor may be integrated into the system to allow the algorithm to adjust $\gamma_T$ as the temperature varies.

Another way in which D can be non-zero is when the speech source is not where it is believed to be—specifically, the angle from the axis of the array to the speech source is incorrect. The distance to the source may be incorrect as well, but that introduces an error in B, not D.

Referring to FIG. 7, it can be seen that for two speech sources (each with their own $d_s$ and $\theta$) that the time difference between the arrival of the speech at $O_1$ and the arrival at $O_2$ is $$\Delta t = \frac{1}{c}(d_{12} - d_{11} - d_{22} + d_{21})$$

where $$d_{11} = \sqrt{d_{S1}^2 - 2d_{S1}d_0\cos(\theta_1) + d_0^2}$$

$$d_{12} = \sqrt{d_{S1}^2 + 2d_{S1}d_0\cos(\theta_1) + d_0^2}$$

$$d_{21} = \sqrt{d_{S2}^2 - 2d_{S2}d_0\cos(\theta_2) + d_0^2}$$

$$d_{22} = \sqrt{d_{S2}^2 + 2d_{S2}d_0\cos(\theta_2) + d_0^2}$$

Figure 26:
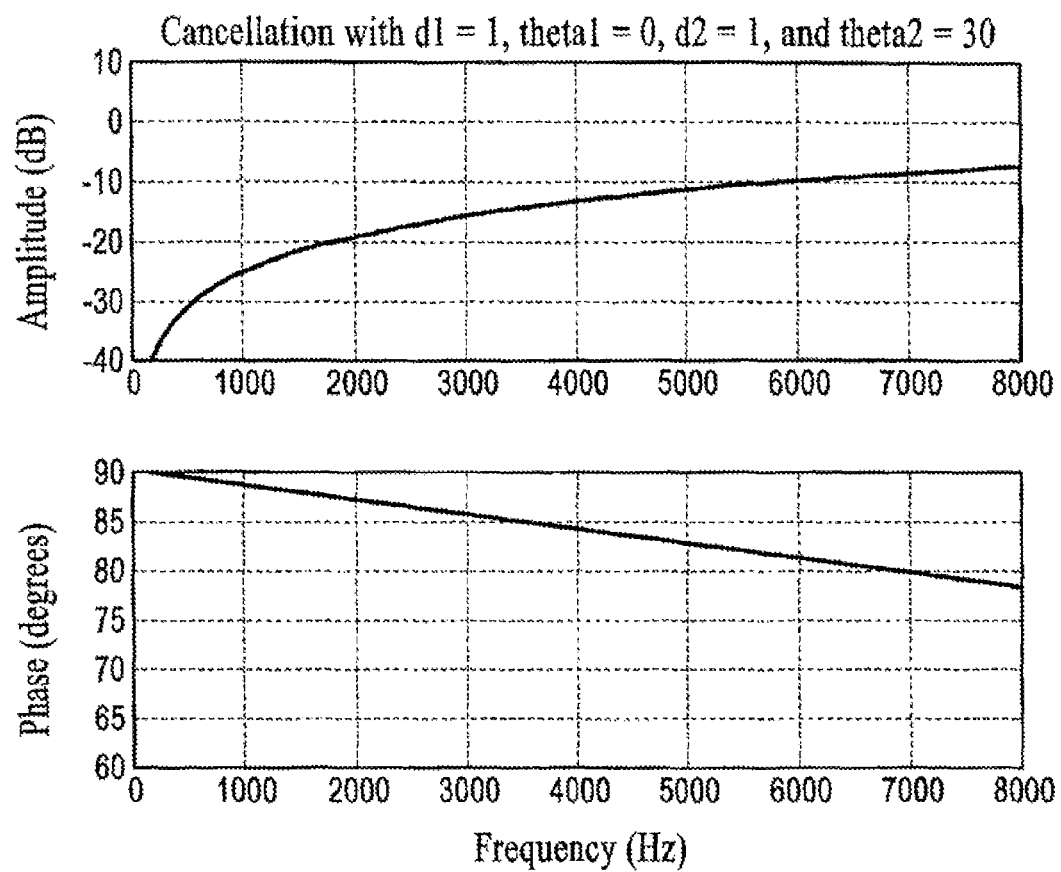
FIG. 26 is a plot of amplitude (top) and phase (bottom) response of the effect on the speech cancellation in $V_2$ due to a mistake in the location of the speech source with theta1=0 degrees and theta2=30 degrees, under an embodiment. The cancellation remains below −10 dB for frequencies below 6 kHz.
Figure 27:
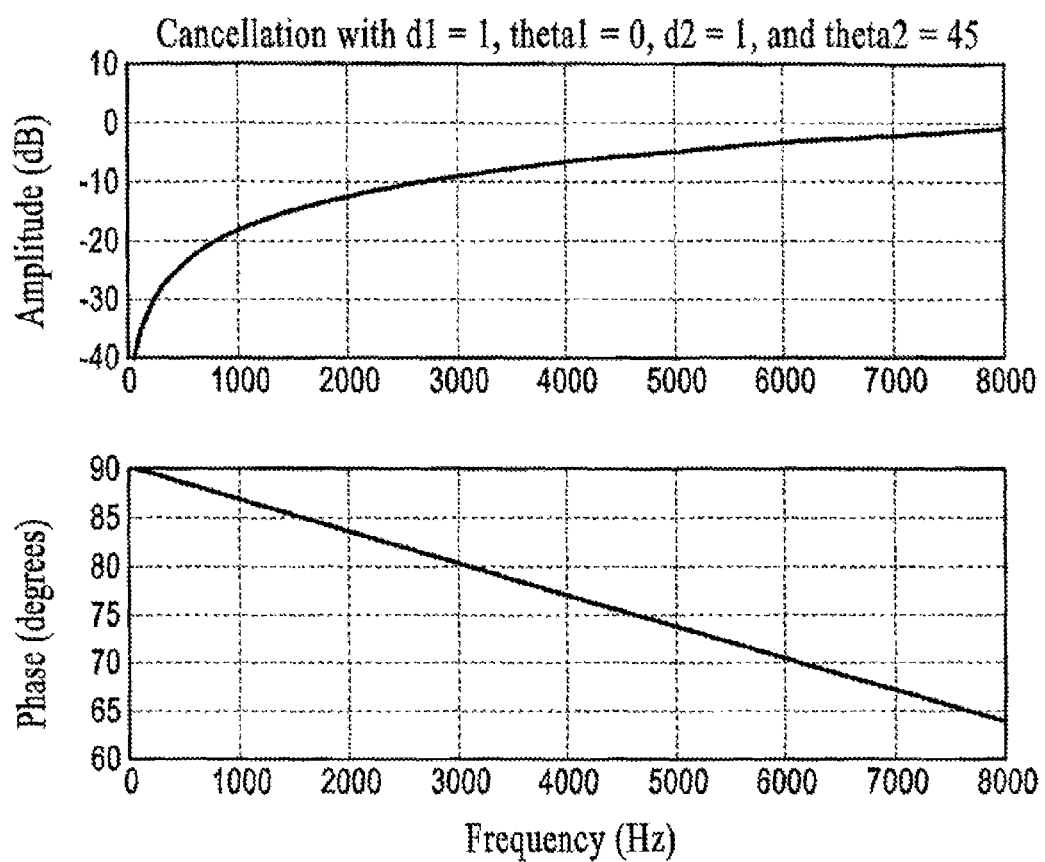
FIG. 27 is a plot of amplitude (top) and phase (bottom) response of the effect on the speech cancellation in $V_2$ due to a mistake in the location of the speech source with theta1=0 degrees and theta2=45 degrees, under an embodiment. The cancellation is below −10 dB for frequencies below about 2.8 kHz and a reduction in performance is expected.

The $V_2$ speech cancellation response for $\theta_1$=0 degrees and $\theta_2$=30 degrees and assuming that B=1 is shown in FIG. 26. FIG. 26 is a plot of amplitude (top) and phase (bottom) response of the effect on the speech cancellation in $V_2$ due to a mistake in the location of the speech source with q1=0 degrees and q2=30 degrees, under an embodiment. Note that the cancellation is still below −10 dB for frequencies below 6 kHz. The cancellation is still below approximately −10 dB for frequencies below approximately 6 kHz, so an error of this type may not significantly affect the performance of the system. However, if $\theta_2$ is increased to approximately 45 degrees, as shown in FIG. 27, the cancellation is below approximately −10 dB for frequencies below approximately 2.8 kHz. FIG. 27 is a plot of amplitude (top) and phase (bottom) response of the effect on the speech cancellation in $V_2$ due to a mistake in the location of the speech source with q1=0 degrees and q2=45 degrees, under an embodiment. Now the cancellation is below −10 dB for frequencies below about 2.8 kHz and a reduction in performance is expected. The poor $V_2$ speech cancellation above approximately 4 kHz may result in significant devoicing for those frequencies.

The description above has assumed that the microphones $O_1$ and $O_2$ were calibrated so that their response to a source located the same distance away was identical for both amplitude and phase. This is not always feasible, so a more practical calibration procedure is presented below. It is not as accurate, but is much simpler to implement. Begin by defining a filter $\alpha(z)$ such that:

$$O_{1C}(z)=\alpha(z)O_{2C}(z)$$

where the "C" subscript indicates the use of a known calibration source. The simplest one to use is the speech of the user. Then $$O_{1S}(z)=\alpha(z)O_{2C}(z)$$

The microphone definitions are now:

$$V_1(z)=O_1(z)\cdot z^{-\gamma}-\beta(z)\alpha(z)O_2(z).$$

$$V_2(z)=\alpha(z)O_2(z)-z^{-\gamma}\beta(z)O_1(z)$$

The $\beta$ of the system should be fixed and as close to the real value as possible. In practice, the system is not sensitive to changes in $\beta$ and errors of approximately +−5% are easily tolerated. During times when the user is producing speech but there is little or no noise, the system can train $\alpha(z)$ to remove as much speech as possible. This is accomplished by:
1. Construct an adaptive system as shown in FIG. 6 with $\beta O_{1S}(z)z^{-\gamma}$ in the "MIC1" position, $O_{2S}(z)$ in the "MIC2" position, and $\alpha(z)$ in the $H_1(z)$ position.
2. During speech, adapt $\alpha(z)$ to minimize the residual of the system.
3. Construct $V_1(z)$ and $V_2(z)$ as above.

A simple adaptive filter can be used for $\alpha(z)$ so that the relationship between the microphones is well modeled. The system of an embodiment trains when speech is being produced by the user. A sensor like the SSM is invaluable in determining when speech is being produced in the absence of noise. If the speech source is fixed in position and may not vary significantly during use (such as when the array is on an earpiece), the adaptation should be infrequent and slow to update in order to minimize any errors introduced by noise present during training.

The above formulation works very well because the noise (far-field) responses of $V_1$ and $V_2$ are very similar while the speech (near-field) responses are very different. However, the formulations for $V_1$ and $V_2$ can be varied and still result in good performance of the system as a whole. If the definitions for $V_1$ and $V_2$ are taken from above and new variables B1 and B2 are inserted, the result is:

$$V_1(z) = O_1(z) \cdot z^{-\gamma T} - B_1 \beta_T O_2(z)$$

$$V_2(z) = O_2(z) - z^{-\gamma T} B_2 \beta_T O_1(z)$$

where B1 and B2 are both positive numbers or zero. If B1 and B2 are set equal to unity, the optimal system results as described above. If B1 is allowed to vary from unity, the response of $V_1$ is affected. An examination of the case where B2 is left at 1 and B1 is decreased follows. As B1 drops to approximately zero, $V_1$ becomes less and less directional, until it becomes a simple omnidirectional microphone when B1=0. Since B2=1, a speech null remains in $V_2$, so very different speech responses remain for $V_1$ and $V_2$. However, the noise responses are much less similar, so denoising may not be as effective. Practically, though, the system still performs well. B1 can also be increased from unity and once again the system may denoise well, just not as well as with B1=1.

If B2 is allowed to vary, the speech null in $V_2$ is affected. As long as the speech null is still sufficiently deep, the system may still perform well. Practically values down to approximately B2=0.6 have shown sufficient performance, but it is recommended to set B2 close to unity for optimal performance.

Similarly, variables $\in$ and $\Delta$ may be introduced so that:

$$V_1(z) = (\in - \beta) O_{2N}(z) + (1 + \Delta) O_{1N}(z) z^{-\gamma}$$

$$V_2(z) = (1 + \Delta) O_{2N}(z) + (\in - \beta) O_{1N}(z) z^{-\gamma}$$

This formulation also allows the virtual microphone responses to be varied but retains the all-pass characteristic of $H_1(z)$.

In conclusion, the system is flexible enough to operate well at a variety of B1 values, but B2 values should be close to unity to limit devoicing for best performance.

Figure 28:
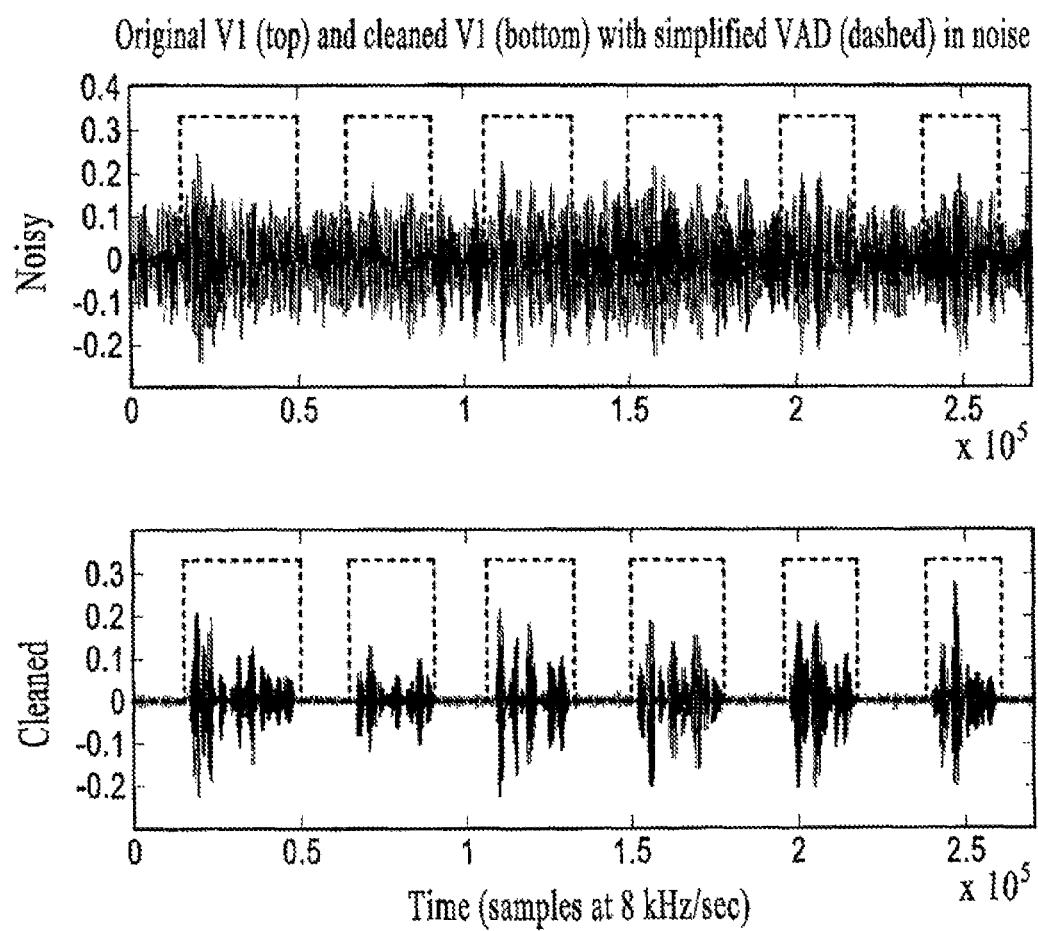
FIG. 28 shows experimental results for a $2d_0$=19 mm array using a linear β of 0.83 on a Bruel and Kjaer Head and Torso Simulator (HATS) in very loud (~85 dBA) music/speech noise environment, under an embodiment. The noise has been reduced by about 25 dB and the speech hardly affected, with no noticeable distortion.

Experimental results for a $2d_0=19$ mm array using a linear $\beta$ of 0.83 and B1=B2=1 on a Bruel and Kjaer Head and Torso Simulator (HATS) in very loud (~85 dBA) music/speech noise environment are shown in FIG. 28. The alternate microphone calibration technique discussed above was used to calibrate the microphones. The noise has been reduced by about 25 dB and the speech hardly affected, with no noticeable distortion. Clearly the technique significantly increases the SNR of the original speech, far outperforming conventional noise suppression techniques.

The DOMA can be a component of a single system, multiple systems, and/or geographically separate systems. The DOMA can also be a subcomponent or subsystem of a single system, multiple systems, and/or geographically separate systems. The DOMA can be coupled to one or more other components (not shown) of a host system or a system coupled to the host system.

One or more components of the DOMA and/or a corresponding system or application to which the DOMA is coupled or connected includes and/or runs under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, cellular telephones, personal digital assistants, portable computing devices, and portable communication devices, but is not so limited. The processing system can include components within a larger computer system.

An acoustic vibration sensor, also referred to as a speech sensing device, is described below. The acoustic vibration sensor is similar to a microphone in that it captures speech information from the head area of a human talker or talker in noisy environments. Previous solutions to this problem have either been vulnerable to noise, physically too large for certain applications, or cost prohibitive. In contrast, the acoustic vibration sensor described herein accurately detects and captures speech vibrations in the presence of substantial airborne acoustic noise, yet within a smaller and cheaper physical package. The noise-immune speech information provided by the acoustic vibration sensor can subsequently be used in downstream speech processing applications (speech enhancement and noise suppression, speech encoding, speech recognition, talker verification, etc.) to improve the performance of those applications.

Figure 30A:
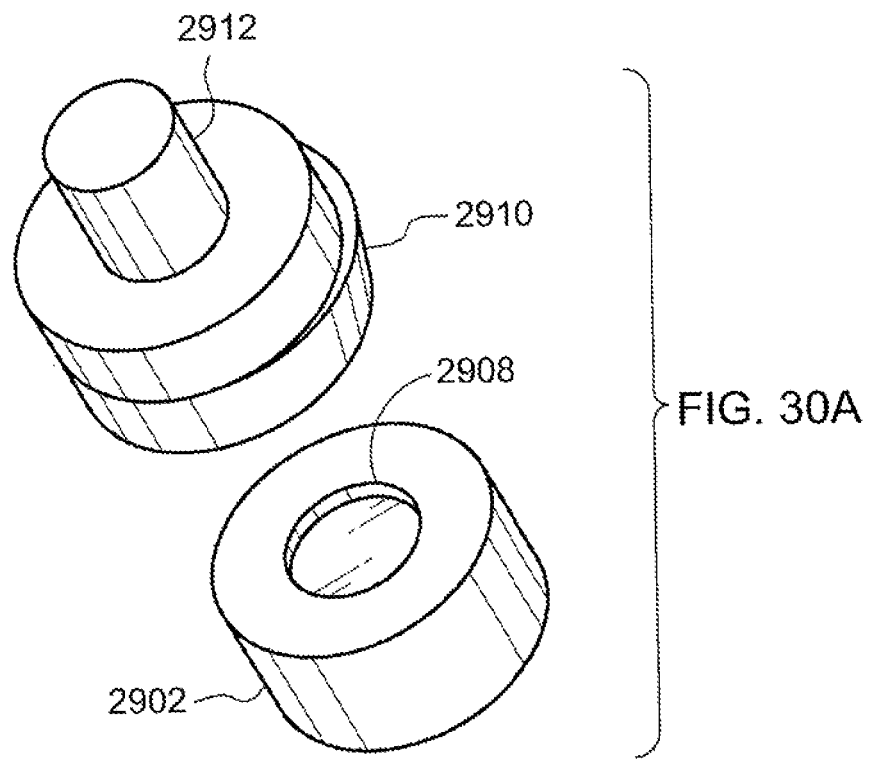
FIG. 30A is an exploded view of an acoustic vibration sensor, under the embodiment of FIG. 29.
Figure 30B:
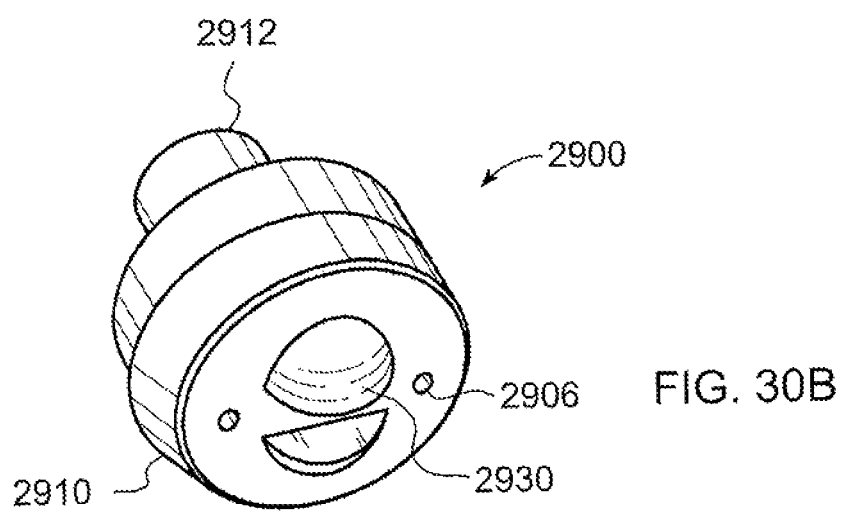
FIG. 30B is perspective view of an acoustic vibration sensor, under the embodiment of FIG. 29.

FIG. 29 is a cross section view of an example of an acoustic vibration sensor 2900, also referred to herein as the sensor 2900, under an embodiment. FIG. 30A is an exploded view of an acoustic vibration sensor 2900, under the embodiment of FIG. 29. FIG. 30B is perspective view of an acoustic vibration sensor 2900, under the embodiment of FIG. 29. The sensor 2900 includes an enclosure 2902 having a first port 2904 on a first side and at least one second port 2906 on a second side of the enclosure 2902. A diaphragm 2908, also referred to as a sensing diaphragm 2908, is positioned between the first and second ports. A coupler 2910, also referred to as the shroud 2910 or cap 2910, forms an acoustic seal around the enclosure 2902 so that the first port 2904 and the side of the diaphragm facing the first port 2904 are isolated from the airborne acoustic environment of the human talker. The coupler 2910 of an embodiment is contiguous, but is not so limited. The second port 2906 couples a second side of the diaphragm to the external environment.

The sensor also includes electret material 2920 and the associated components and electronics coupled to receive acoustic signals from the talker via the coupler 2910 and the diaphragm 2908 and convert the acoustic signals to electrical signals representative of human speech. Electrical contacts 2930 provide the electrical signals as an output. Alternative embodiments can use any type/combination of materials and/or electronics to convert the acoustic signals to electrical signals representative of human speech and output the electrical signals.

The coupler 2910 of an embodiment is formed using materials having acoustic impedances matched to the impedance of human skin (characteristic acoustic impedance of skin is approximately $1.5 \times 10^6$ Paxs/m). The coupler 2910 therefore, is formed using a material that includes at least one of silicone gel, dielectric gel, thermoplastic elastomers (TPE), and rubber compounds, but is not so limited. As an example, the coupler 2910 of an embodiment is formed using Kraiburg TPE products. As another example, the coupler 2910 of an embodiment is formed using Sylgard® Silicone products.

The coupler 2910 of an embodiment includes a contact device 2912 that includes, for example, a nipple or protrusion that protrudes from either or both sides of the coupler 2910. In operation, a contact device 2912 that protrudes from both sides of the coupler 2910 includes one side of the contact device 2912 that is in contact with the skin surface of the talker and another side of the contact device 2912 that is in contact with the diaphragm, but the embodiment is not so limited. The coupler 2910 and the contact device 2912 can be formed from the same or different materials.

The coupler 2910 transfers acoustic energy efficiently from skin/flesh of a talker to the diaphragm, and seals the diaphragm from ambient airborne acoustic signals. Consequently, the coupler 2910 with the contact device 2912 efficiently transfers acoustic signals directly from the talker's body (speech vibrations) to the diaphragm while isolating the diaphragm from acoustic signals in the airborne environment of the talker (characteristic acoustic impedance of air is approximately 415 Paxs/m). The diaphragm is isolated from acoustic signals in the airborne environment of the talker by the coupler 2910 because the coupler 2910 prevents the signals from reaching the diaphragm, thereby reflecting and/or dissipating much of the energy of the acoustic signals in the airborne environment. Consequently, the sensor 2900 responds primarily to acoustic energy transferred from the skin of the talker, not air. When placed against the head of the talker, the sensor 2900 picks up speech-induced acoustic signals on the surface of the skin while airborne acoustic noise signals are largely rejected, thereby increasing the signal-to-noise ratio and providing a very reliable source of speech information.

Performance of the sensor 2900 is enhanced through the use of the seal provided between the diaphragm and the airborne environment of the talker. The seal is provided by the coupler 2910. A modified gradient microphone is used in an embodiment because it has pressure ports on both ends. Thus, when the first port 2904 is sealed by the coupler 2910, the second port 2906 provides a vent for air movement through the sensor 2900.

FIG. 31 is a schematic diagram of a coupler 2910 of an acoustic vibration sensor, under the embodiment of FIG. 29. The dimensions shown are in millimeters and are intended to serve as an example for one embodiment. Alternative embodiments of the coupler can have different configurations and/or dimensions. The dimensions of the coupler 2910 show that the acoustic vibration sensor 2900 is small in that the sensor 2900 of an embodiment is approximately the same size as typical microphone capsules found in mobile communication devices. This small form factor allows for use of the sensor 2910 in highly mobile miniaturized applications, where some example applications include at least one of cellular telephones, satellite telephones, portable telephones, wireline telephones, Internet telephones, wireless transceivers, wireless communication radios, personal digital assistants (PDAs), personal computers (PCs), headset devices, head-worn devices, and earpieces.

The acoustic vibration sensor provides very accurate Voice Activity Detection (VAD) in high noise environments, where high noise environments include airborne acoustic environments in which the noise amplitude is as large if not larger than the speech amplitude as would be measured by conventional omnidirectional microphones. Accurate VAD information provides significant performance and efficiency benefits in a number of important speech processing applications including but not limited to: noise suppression algorithms such as the Pathfinder algorithm available from AliphCom of San Francisco, Calif. and described in the Related Applications; speech compression algorithms such as the Enhanced Variable Rate Coder (EVRC) deployed in many commercial systems; and speech recognition systems.

In addition to providing signals having an improved signal-to-noise ratio, the acoustic vibration sensor uses minimal power to operate (on the order of 200 micro Amps, for example). In contrast to alternative solutions that require power, filtering, and/or significant amplification, the acoustic vibration sensor uses a standard microphone interface to connect with signal processing devices. The use of the standard microphone interface avoids the additional expense and size of interface circuitry in a host device and supports for of the sensor in highly mobile applications where power usage is an issue.

Figure 32:
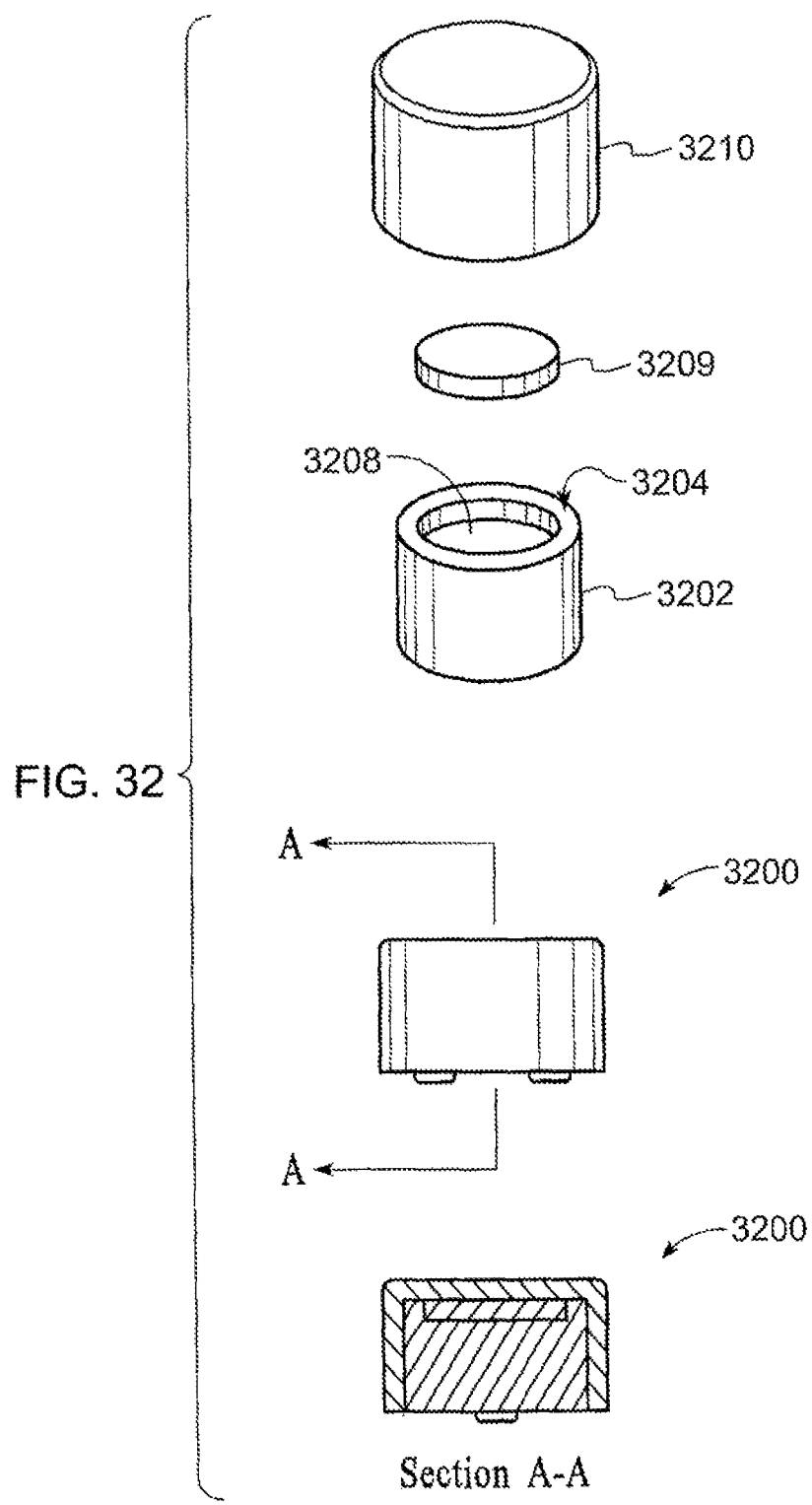
FIG. 32 is an exploded view of an acoustic vibration sensor, under an alternative embodiment.

FIG. 32 is an exploded view of an acoustic vibration sensor 3200, under an alternative embodiment. The sensor 3200 includes an enclosure 3202 having a first port 3204 on a first side and at least one second port (not shown) on a second side of the enclosure 3202. A diaphragm 3208 is positioned between the first and second ports. A layer of silicone gel 3209 or other similar substance is formed in contact with at least a portion of the diaphragm 3208. A coupler 3210 or shroud 3210 is formed around the enclosure 3202 and the silicon gel 3209 where a portion of the coupler 3210 is in contact with the silicon gel 3209. The coupler 3210 and silicon gel 3209 in combination form an acoustic seal around the enclosure 3202 so that the first port 3204 and the side of the diaphragm facing the first port 3204 are isolated from the acoustic environment of the human talker. The second port couples a second side of the diaphragm to the acoustic environment.

As described above, the sensor includes additional electronic materials as appropriate that couple to receive acoustic signals from the talker via the coupler 3210, the silicon gel 3209, and the diaphragm 3208 and convert the acoustic signals to electrical signals representative of human speech. Alternative embodiments can use any type/combination of materials and/or electronics to convert the acoustic signals to electrical signals representative of human speech.

The coupler 3210 and/or gel 3209 of an embodiment are formed using materials having impedances matched to the impedance of human skin. As such, the coupler 3210 is formed using a material that includes at least one of silicone gel, dielectric gel, thermoplastic elastomers (TPE), and rubber compounds, but is not so limited. The coupler 3210 transfers acoustic energy efficiently from skin/flesh of a talker to the diaphragm, and seals the diaphragm from ambient airborne acoustic signals. Consequently, the coupler 3210 efficiently transfers acoustic signals directly from the talker's body (speech vibrations) to the diaphragm while isolating the diaphragm from acoustic signals in the airborne environment of the talker. The diaphragm is isolated from acoustic signals in the airborne environment of the talker by the silicon gel 3209/coupler 3210 because the silicon gel 3209/coupler 3210 prevents the signals from reaching the diaphragm, thereby reflecting and/or dissipating much of the energy of the acoustic signals in the airborne environment. Consequently, the sensor 3200 responds primarily to acoustic energy transferred from the skin of the talker, not air. When placed again the head of the talker, the sensor 3200 picks up speech-induced acoustic signals on the surface of the skin while airborne acoustic noise signals are largely rejected, thereby increasing the signal-to-noise ratio and providing a very reliable source of speech information.

Figure 33:
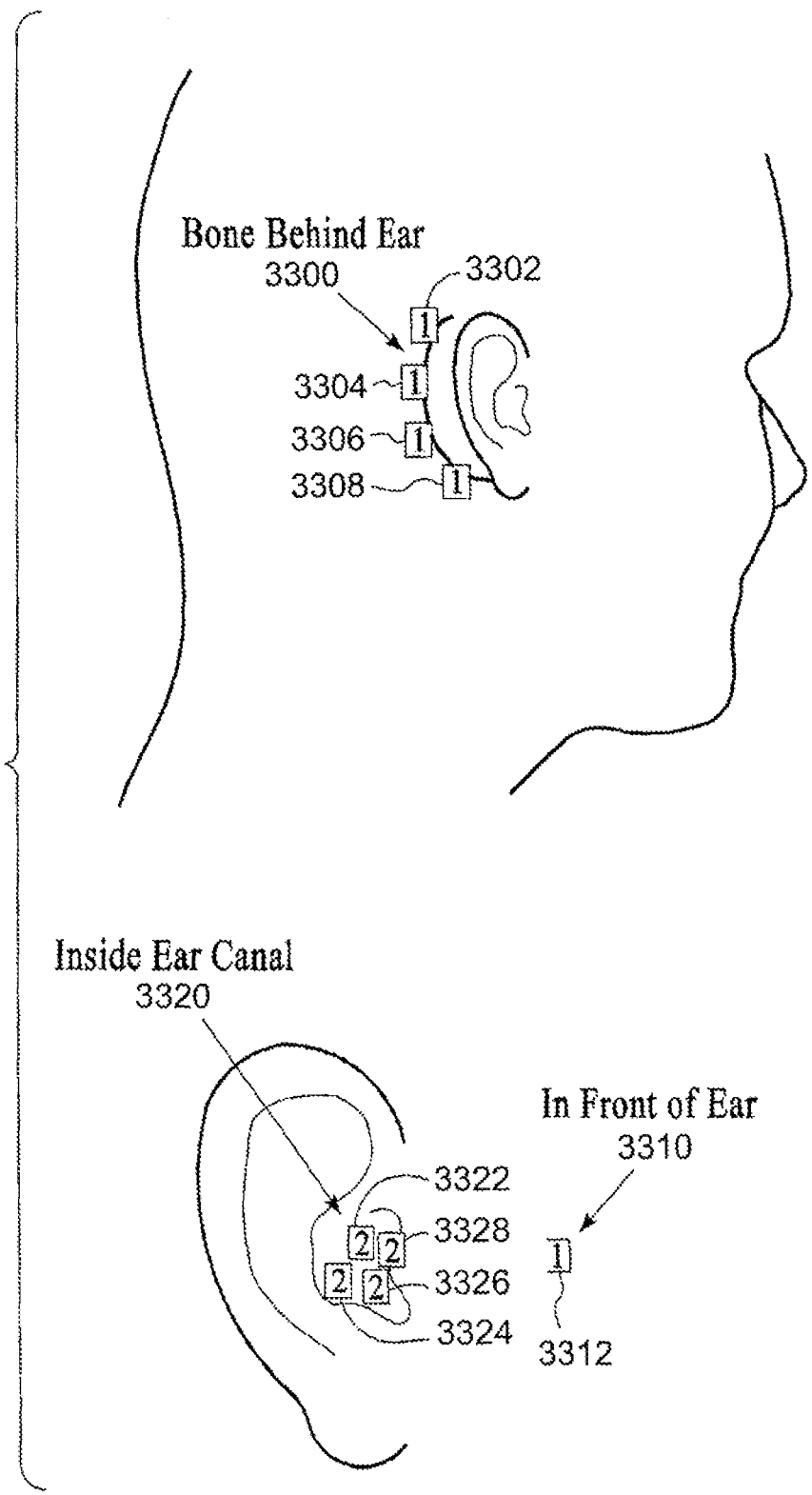
FIG. 33 shows representative areas of sensitivity on the human head appropriate for placement of the acoustic vibration sensor, under an embodiment.

There are many locations outside the ear from which the acoustic vibration sensor can detect skin vibrations associated with the production of speech. The sensor can be mounted in a device, handset, or earpiece in any manner, as long as reliable skin contact is used to detect the skin-borne vibrations associated with the production of speech. FIG. 33 shows representative areas of sensitivity 3300-3328 on the human head appropriate for placement of an example of an acoustic vibration sensor 2900/3200, under an embodiment. The areas of sensitivity 3300-3320 include numerous locations 3302-3308 in an area behind the ear 3300, at least one location 3312 in an area in front of the car 3310, and in numerous locations 3322-3328 in the car canal area 3320. The areas of sensitivity 3300-3328 are the same for both sides of the human head. These representative areas of sensitivity 3300-3320 are provided as examples and do not limit the embodiments described herein to use in these areas.

Figure 34:
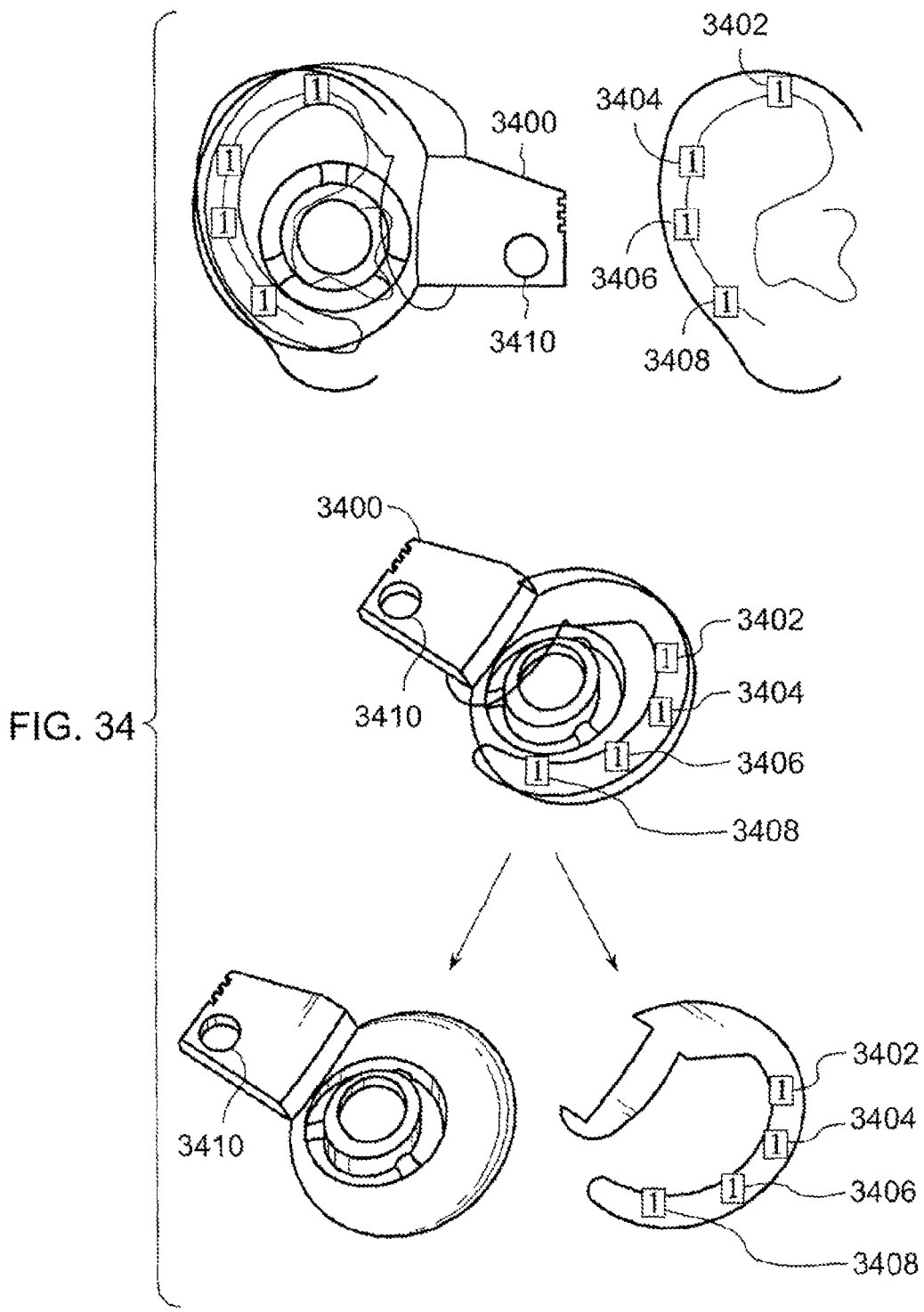
FIG. 34 is a generic headset device that includes an acoustic vibration sensor placed at any of a number of locations, under an embodiment.

FIG. 34 is a generic headset device 3400 that includes an acoustic vibration sensor 2900/3200 placed at any of a number of locations 3402-3408, under an embodiment. Generally, placement of the acoustic vibration sensor 2900/3200 can be on any part of the device 3400 that corresponds to the areas of sensitivity 3300-3328 (FIG. 33) on the human head. While a headset device is shown as an example, any number of communication devices known in the art can carry and/or couple to an acoustic vibration sensor 2900/3200.

FIG. 35 is a diagram of a manufacturing method 3500 for an acoustic vibration sensor, under an embodiment. Operation begins with, for example, a uni-directional microphone 3520, at block 3502. Silicon gel 3522 is formed over/on the diaphragm (not shown) and the associated port, at block 3504. A material 3524, for example polyurethane film, is formed or placed over the microphone 3520/silicone gel 3522 combination, at block 3506, to form a coupler or shroud. A snug fit collar or other device is placed on the microphone to secure the material of the coupler during curing, at block 3508.

Note that the silicon gel (block 3502) is an optional component that depends on the embodiment of the sensor being manufactured, as described above. Consequently, the manufacture of an acoustic vibration sensor 2900 that includes a contact device 2912 (referring to FIG. 29) may not include the formation of silicon gel 3522 over/on the diaphragm. Further, the coupler formed over the microphone for this sensor 2900 may include the contact device 2912 or formation of the contact device 2912.

The systems and methods described herein include and/or run under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, cellular telephones, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein refers to any logic processing unit, such as one or more central processing units (CPUs), digital signal processors (DSPs), application-specific integrated circuits (ASIC), etc. The processor and memory can be monolithically integrated onto a single chip, distributed among a number of chips or components of a host system, and/or provided by some combination of algorithms. The methods described herein can be implemented in one or more of software algorithm(s), programs, firmware, hardware, components, circuitry, in any combination.

System components embodying the systems and methods described herein can be located together or in separate locations. Consequently, system components embodying the systems and methods described herein can be components of a single system, multiple systems, and/or geographically separate systems. These components can also be subcomponents or subsystems of a single system, multiple systems, and/or geographically separate systems. These components can be coupled to one or more other components of a host system or a system coupled to the host system.

Communication paths couple the system components and include any medium for communicating or transferring files among the components. The communication paths include wireless connections, wired connections, and hybrid wireless/wired connections. The communication paths also include couplings or connections to networks including local area networks (MANs), wide area networks (WANs), proprietary networks, interoffice or backend networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

Unless the context clearly indicates otherwise, throughout the description, the words "comprise," "comprising," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments is not intended to be exhaustive or to limit the systems and methods described to the precise form disclosed. While specific embodiments and examples are described herein for illustrative purposes, various equivalent modifications are possible within the scope of other systems and methods, as those skilled in the relevant art may recognize. The teachings provided herein can be applied to other processing systems and methods, not only for the systems and methods described above.

The elements and acts of the various embodiments described above can be combined to provide further embodiments. These and other changes can be made to the embodiments in light of the above detailed description.

What is claimed:

1. A method, comprising:
   measuring an amount of energy reflected by an interface using a light emitter and detector when a surface skin microphone (SSM) boot of a SSM is not in contact with skin, the SSM including a diaphragm coupled with a vibration transducer and the SSM boot;
   measuring another amount of energy reflected by another interface using the light emitter and detector when the SSM boot is in contact with the skin; and
   detecting skin contact by detecting a change between the amount of energy and the another amount of energy using a digital signal processor.

2. The method of claim 1, wherein the amount of energy is greater than the another amount of energy.

3. The method of claim 1, further comprising detecting speech after detecting the skin contact.

4. The method of claim 1, wherein the energy comprises infrared light energy transmitted using infrared spectra.

5. The method of claim 1, wherein an index of refraction of the SSM boot is less than and almost equal to another index of refraction of the skin.

6. The method of claim 1, wherein the light emitter and detector comprises an infrared light-emitting diode pair.

7. The method of claim 1, wherein the interface is between the SSM boot and air.

8. The method of claim 1, wherein the another interface is between the SSM boot and the skin.

9. The method of claim 1, wherein the SSM boot comprises a material having an index of refraction greater than or equal to another index of refraction of air.

10. The method of claim 1, wherein the SSM boot comprises a material having an index of refraction greater than or equal to an air index of refraction and less than or equal to another index of refraction of the skin.

11. The method of claim 1, wherein the detecting the change between the amount of energy and the another amount of energy is performed after a critical angle is increased.

12. The method of claim 1, wherein the detecting the change between the amount of energy and the another amount of energy is performed after a critical angle is eliminated.

13. The method of claim 1, wherein the light emitter and detector are coupled with a side of the SSM boot, and the SSM boot comprises a material that is optically transmissive to infrared light emitted by the light emitter and detector.

14. The method of claim 1, wherein the vibration transducer includes a coupler having a contact device protruding from a side of the coupler.

15. The method of claim 1, wherein the diaphragm is positioned between a contact device and an electret material, the electret material in contact with a backplate, the contact device protruding from a side of a coupler.

16. The method of claim 1, wherein the vibration transducer includes a coupler having an acoustic impedance matched to an impedance of human skin.

* * * * *